United States Patent
Meyers et al.

(10) Patent No.: US 12,390,407 B2
(45) Date of Patent: Aug. 19, 2025

(54) PERSONAL CLEANSING COMPOSITIONS, METHODS AND USES

(71) Applicant: The Procter & Gamble Company, Cincinnati, OH (US)

(72) Inventors: Jessa Leigh Meyers, Cincinnati, OH (US); Edward Dewey Smith, III, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 380 days.

(21) Appl. No.: 16/522,739

(22) Filed: Jul. 26, 2019

(65) Prior Publication Data

US 2020/0030208 A1 Jan. 30, 2020

(30) Foreign Application Priority Data

Jul. 26, 2018 (EP) .................................. 18185894

(51) Int. Cl.
| | |
|---|---|
| A61K 8/46 | (2006.01) |
| A61K 8/44 | (2006.01) |
| A61K 8/73 | (2006.01) |
| A61Q 5/02 | (2006.01) |
| A61Q 19/00 | (2006.01) |

(52) U.S. Cl.
CPC ............... *A61K 8/466* (2013.01); *A61K 8/44* (2013.01); *A61K 8/731* (2013.01); *A61K 8/736* (2013.01); *A61Q 5/02* (2013.01); *A61Q 19/00* (2013.01); *A61K 2800/30* (2013.01)

(58) Field of Classification Search
None
See application file for complete search history.

(56) References Cited

U.S. PATENT DOCUMENTS

| | | | |
|---|---|---|---|
| 4,954,282 A | 9/1990 | Rys | |
| 5,246,613 A | 9/1993 | Gilbert | |
| 5,415,810 A | 5/1995 | Lee | |
| 5,785,979 A * | 7/1998 | Wells | A61P 17/00 |
| | | | 424/401 |
| 5,962,395 A | 10/1999 | Puvvada | |
| 6,007,816 A | 12/1999 | St John | |
| 6,451,333 B1 | 9/2002 | Beerse et al. | |
| 6,565,863 B1 | 5/2003 | Guillou | |
| 7,655,607 B2 | 2/2010 | Tsaur | |
| 7,659,235 B2 | 2/2010 | Tsaur | |
| 7,671,000 B2 | 3/2010 | Tsaur | |
| 7,674,759 B2 | 3/2010 | Tsaur | |
| 7,807,612 B2 | 10/2010 | Tsaur | |
| 7,879,780 B2 | 2/2011 | Tsaur | |
| 8,105,994 B2 | 1/2012 | Tsaur | |
| 8,124,574 B2 | 2/2012 | Tsaur | |
| 8,187,581 B2 | 5/2012 | Loeffler et al. | |
| 8,263,538 B2 | 9/2012 | Tsaur | |
| 8,268,767 B2 | 9/2012 | Tsaur et al. | |
| 8,772,212 B2 | 7/2014 | Restrepo et al. | |
| 8,980,239 B2 | 3/2015 | Staudigel et al. | |
| 9,066,859 B1 | 6/2015 | Rizk | |
| 9,187,716 B2 | 11/2015 | Griffin et al. | |
| 9,216,147 B2 | 12/2015 | Fahl | |
| 9,655,821 B2 | 5/2017 | Carter et al. | |
| 9,724,283 B2 | 8/2017 | Rizk | |
| 9,895,300 B2 | 2/2018 | Schroeder | |
| 10,039,939 B2 | 8/2018 | Xavier | |
| 10,265,257 B2 | 4/2019 | Cotrell | |
| 10,912,719 B2 | 2/2021 | Gulbin | |
| 11,638,683 B2 | 5/2023 | Meyers et al. | |
| 2003/0223951 A1 | 12/2003 | Geary et al. | |
| 2004/0224863 A1 | 11/2004 | Sun | |
| 2005/0090422 A1 | 4/2005 | Lukenbach et al. | |
| 2005/0143268 A1 | 6/2005 | Midha et al. | |
| 2005/0239670 A1 | 10/2005 | Stella et al. | |
| 2008/0153729 A1 | 6/2008 | Tsaur et al. | |
| 2008/0153730 A1 | 6/2008 | Tsaur et al. | |

(Continued)

FOREIGN PATENT DOCUMENTS

| | | |
|---|---|---|
| CA | 2068423 A1 | 6/1991 |
| CN | 104095771 A | 10/2014 |

(Continued)

OTHER PUBLICATIONS

All final and non-final office actions for U.S. Appl. No. 16/522,739.
European Search Report for EP18185892.9 dated Dec. 19, 2018.
European Search Report for EP18185894.5 dated Dec. 19, 2018.
PCT International Search Report and Written Opinion for PCT/US2019/040219, mailed Oct. 16, 2019.
PCT International Search Report and Written Opinion for PCT/US2019/040234 dated Sep. 19, 2019.
All Office Actions; U.S. Appl. No. 17/945,178, filed Sep. 15, 2022.
Carnali, J.O. "A dispersed anisotropic phase as the origin of the weak-gel properties of aqueous xanthan gum", Journal of applied polymer science vol. 43, Year: 1991, pp. 929-941.
Mintel Record ID 3197361, online retrieved from, "http;//www.gnpd.com", No Known date, 04 pages.

*Primary Examiner* — Tigabu Kassa
(74) *Attorney, Agent, or Firm* — Alexandra S. Anoff

(57) ABSTRACT

A personal cleansing composition includes: (a) a surfactant system, wherein the surfactant system includes: from about 0.1% to about 5%, of a fatty acyl isethionate surfactant; from about 0.5% to about 40%, of a co-surfactant, wherein the co-surfactant is selected from the group consisting of an anionic surfactant being not an isethionate surfactant, a non-ionic surfactant, an amphoteric surfactant, a zwitterionic surfactant, and mixtures thereof; (b) from about 0.05% to about 5%, of a natural polysaccharide, a chemically modified natural polysaccharide, or a combination thereof; wherein the personal cleansing composition includes a first and second phase, wherein the first phase is an isotropic and micellar surfactant phase; wherein the second phase is a polymer liquid crystalline phase which includes polymer liquid crystals of the natural polysaccharide, the chemically modified natural polysaccharide, or the combination.

7 Claims, 9 Drawing Sheets

(56) References Cited

U.S. PATENT DOCUMENTS

| | | |
|---|---|---|
| 2009/0062177 A1 | 3/2009 | Tsaur |
| 2010/0266516 A1 | 10/2010 | Cotrell |
| 2011/0117225 A1 | 5/2011 | Wei et al. |
| 2011/0280822 A1 | 11/2011 | Griffin et al. |
| 2012/0122755 A1 | 5/2012 | Andjelic et al. |
| 2013/0156715 A1 | 6/2013 | Hall |
| 2014/0161755 A1 | 6/2014 | Arora |
| 2014/0228263 A1 | 8/2014 | Okazaki |
| 2014/0228268 A1 | 8/2014 | Fahl et al. |
| 2016/0095804 A1 | 4/2016 | Xavier et al. |
| 2016/0128913 A1 | 5/2016 | Wei et al. |
| 2016/0287504 A1 | 10/2016 | Schroeder et al. |
| 2016/0310391 A1 | 10/2016 | Smith et al. |
| 2017/0247646 A1 | 8/2017 | Detroch et al. |
| 2017/0304173 A1 | 10/2017 | Elder et al. |
| 2018/0098923 A1 | 4/2018 | Hutton, III |
| 2018/0116937 A1* | 5/2018 | Park ................... A61K 8/466 |
| 2018/0280269 A1 | 10/2018 | Rughani et al. |
| 2018/0318195 A1 | 11/2018 | Blachechen et al. |
| 2020/0022891 A1 | 1/2020 | Yang et al. |
| 2020/0030208 A1 | 1/2020 | Meyers |
| 2020/0030220 A1 | 1/2020 | Meyers |
| 2020/0283555 A1 | 9/2020 | Hsu et al. |
| 2023/0024593 A1 | 1/2023 | Meyers et al. |
| 2023/0329993 A1 | 10/2023 | Zhang |
| 2024/0335366 A1 | 10/2024 | Zhang |

FOREIGN PATENT DOCUMENTS

| | | |
|---|---|---|
| CN | 106619220 A | 5/2017 |
| CN | 106691890 A | 5/2017 |
| CN | 107822945 A | 3/2018 |
| CN | 110054780 A | 7/2019 |
| DE | 102014225606 A1 | 10/2015 |
| EP | 2682161 A2 | 1/2014 |
| EP | 2094228 B1 | 5/2017 |
| WO | 9631187 A2 | 10/1996 |
| WO | 9813022 A1 | 4/1998 |
| WO | 0064410 A1 | 11/2000 |
| WO | 2010069500 A1 | 6/2010 |
| WO | 2011120780 A2 | 10/2011 |
| WO | 2012022552 A1 | 2/2012 |
| WO | 2015040488 A2 | 3/2015 |
| WO | 2017189493 A1 | 11/2017 |
| WO | 2018157974 A1 | 9/2018 |
| WO | 2019193109 A1 | 10/2019 |

\* cited by examiner

Repeating units of cellulose

Structure of methylcellulose

Structure of carboxymethylcellulose

Structure of mannans

Structure of galactomannans

Structure of xyloglucans

Structure of arabinoxylans

Structure of arabinogalactans

Structure of mixed-linkage (1→3)(1→4) β-D-glucans

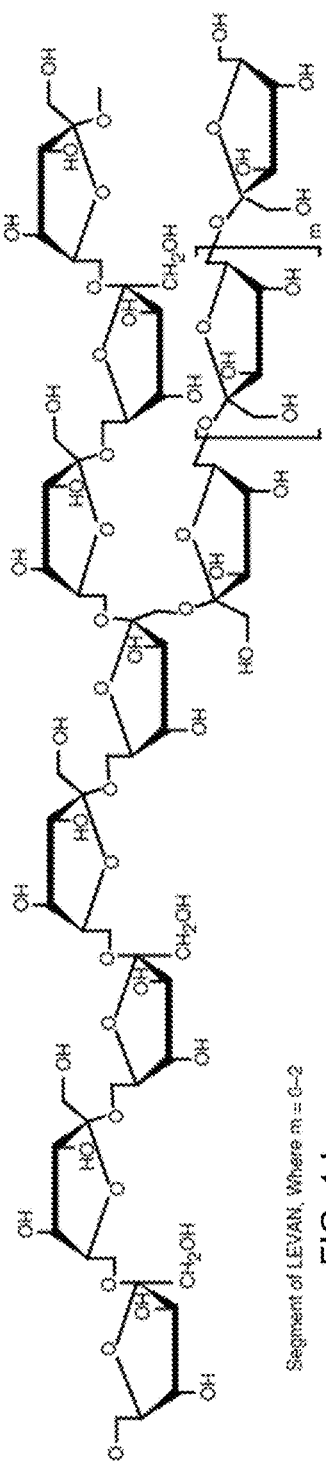
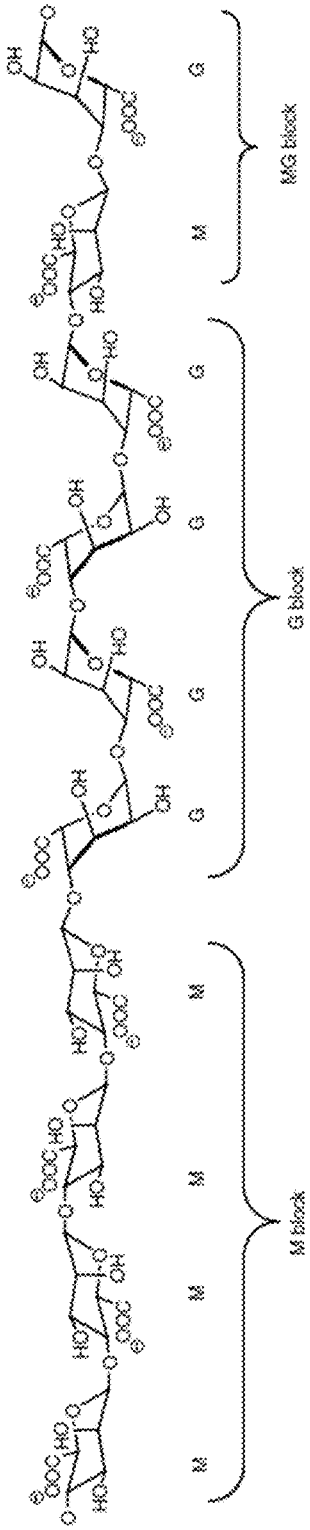
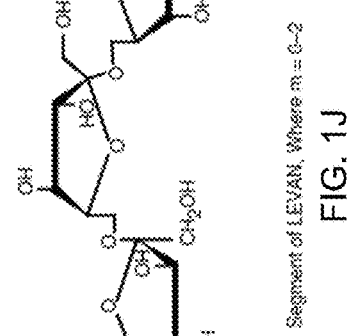
Segment of LEVAN, Where m = 0-2
FIG. 1J
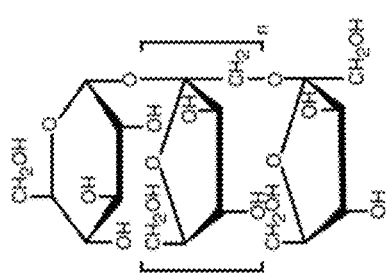
INULIN, Where n = 20-90
FIG. 1I
Structural features of alginates
FIG. 1K

PERSONAL CLEANSING COMPOSITIONS, METHODS AND USES

FIELD OF THE INVENTION

The present application generally relates to personal cleansing compositions, methods of making such compositions, and their uses. The personal cleansing compositions can have desirable rheologic properties and structure when the personal cleansing composition has a surfactant system comprising a fatty acyl isethionate surfactant and when the personal cleansing composition is free of alkyl sulfate and alkyl ether sulfate type of surfactants.

BACKGROUND OF THE INVENTION

Personal cleansing compositions have been traditionally marketed in a variety of forms such as bar soaps, creams, lotions, and gels. Typically, these products must satisfy a number of criteria to be acceptable to consumers. These criteria include cleansing effectiveness, skin feel, mildness to skin, hair, and ocular mucosae, and lather volume. Ideal personal cleansers should gently cleanse the skin or hair, cause little or no irritation, and should not leave the skin or hair overly dry after frequent use.

Anionic surfactants are widely used in personal cleansing compositions. Many of these anionic surfactants contain elongated micelles and are viscoelastic, which is of great importance, especially in the design of shampoos and body washes. In most personal cleansing compositions, alkyl sulfate and alkyl ether sulfate as the anionic surfactants predominate.

The formulation of environmentally friendly personal cleansing compositions is becoming a major challenge for satisfying a new expectation of consumers, in particular that of ecologically designed and/or natural products. It becomes necessary to propose personal cleansing compositions free of alkyl sulfate and alkyl ether sulfate, which have good cosmetic qualities, mainly in terms of viscosity and lather.

Consumers prefer sulfate-free personal cleansing compositions due to perceived mildness and desirable sensorial experience. However, sulfate-free personal cleansing compositions are difficult to thicken sufficiently to afford the user good usage qualities. Two approaches are leveraged to attempt to thicken such formulas. One approach for instance is to use high levels of surfactants to benefit from the self-assembling properties of such ingredients. This approach is most common but it is also costly. The second approach for instance is to use high levels of rheology modifiers which can adversely impact the properties of the composition such as by decreasing the foam and ease of distribution of the composition.

There is a need today to provide personal cleansing products that comprise alternative mild surfactant systems with relatively improved ecotoxic or ecologically friendly environmental profile.

Personal cleansing compositions having a surfactant system comprising a fatty acyl isethionate surfactant and being free of alkyl sulfate and alkyl ether sulfate type of surfactants have been developed. Fatty acyl isethionates are mild anionic surfactants highly desirable in personal cleansing products for hair or skin, because fatty acyl isethionates can lather well, are mild to the skin and have good emollient properties.

However, fatty acyl isethionates are not readily used in liquid personal cleansing compositions, because of their relatively low solubility in water. This may result in unstable personal cleansing compositions which can exhibit inconsistent rheology profiles.

Hence, there is still a need to provide a personal cleansing composition comprising a fatty acyl isethionate surfactant and being free of alkyl sulfate and alkyl ether sulfate type of surfactants and having a satisfactory consistent rheology profile.

Thus, there remains a need for a personal cleansing composition, which is effective at cleaning even while containing lower number of active surfactants than typical cleansing products, but also still possesses good esthetic properties such as good foam, and is thick and creamy in texture, is silky to the touch and affords conditioning.

Benefit agents in the form of solid particles, liquid droplets are of interest for personal cleansing compositions. Benefit agents can be used as pigments or coloring agents, opacifiers, pearlescent agents, feel modifiers, oil absorbers, skin protectants, matting agents, friction enhancers, slip agents, conditioning agents, exfoliants, odor absorbers, or cleaning enhancers. Thus, there is still a need to provide a personal cleansing composition comprising a fatty acyl isethionate surfactant imparted with a sufficient structure to hold benefit agents such as solid particles, liquid droplets.

SUMMARY OF THE INVENTION

An exemplary personal cleansing composition comprises: (a) a surfactant system, wherein the surfactant system comprises: from about 0.1% to about 5%, of a fatty acyl isethionate surfactant by weight of the composition; from about 0.5% to about 40%, of a co-surfactant by weight of the composition, wherein the co-surfactant is selected from the group consisting of an anionic surfactant being not an isethionate surfactant, a non-ionic surfactant, an amphoteric surfactant, a zwitterionic surfactant, and mixtures thereof; (b) from about 0.05% to about 5%, of a natural polysaccharide, a chemically modified natural polysaccharide, or a combination thereof, by weight of the composition; wherein the personal cleansing composition comprises a first and second phase, wherein the first phase is an isotropic and micellar surfactant phase; wherein the second phase is a polymer liquid crystalline phase; wherein the polymer liquid crystalline phase comprises polymer liquid crystals comprising the natural polysaccharide, the chemically modified natural polysaccharide, or the combination; and wherein the composition is free of from alkyl sulfate and alkyl ether sulfate type of surfactants.

An exemplary method for making a personal cleansing composition comprises: (a) providing a surfactant system, wherein the surfactant system comprises: from about 0.1% to about 5%, of a fatty acyl isethionate surfactant by weight of the composition; from about 0.5% to about 40%, of a co-surfactant, wherein the co-surfactant is selected from the group consisting of an anionic surfactant being not an isethionate surfactant, a non-ionic surfactant, an amphoteric surfactant, a zwitterionic surfactant and mixtures thereof, by weight of the composition; (b) adding from about 0.05% to about 5%, of a natural polysaccharide, a chemically modified natural polysaccharide, or a combination thereof, by weight of the composition, to the surfactant system without milling.

BRIEF DESCRIPTION OF THE DRAWINGS

While the specification concludes with claims particularly pointing out and distinctly claiming an invention, it is believed that the same will be better understood from the following description read in conjunction with the accompanying drawings in which:

FIG. 1I is related to the structure of inulin;

FIG. 1J is related to the structure of levan;

FIG. 1K is related to the structural features of alginates;

DETAILED DESCRIPTION OF THE INVENTION

Definitions and General

Figure 1A:
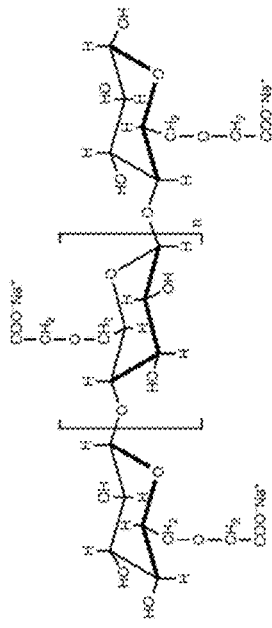
FIG. 1A represents the repeating units of cellulose.

In this document, the following definitions apply unless specifically stated otherwise.

All percentages are by weight (w/w) of the respective composition, unless otherwise specified. All ratios or percentages are weight ratios or weight percentages unless specifically stated otherwise. "% wt." means percentage by weight. References to "parts" e.g. a mixture of 1 part X and 3 parts Y, is a ratio by weight. When more than one composition is used during a treatment, the total weight to be considered is the total weight of all the compositions applied on the hair or skin simultaneously (i.e. the weight found "on head"), unless otherwise specified.

"QSP" or "q.s." means sufficient quantity for 100% or for 100 g. "+/−" indicates the standard deviation. All ranges are inclusive and combinable. The number of significant digits conveys neither a limitation on the indicated amount nor on the accuracy of the measurement.

All measurements are understood to be made at 20° C. and at ambient conditions, where "ambient conditions" means at 1 atmosphere (atm) of pressure and at 65% relative humidity, unless otherwise stated. "Relative humidity" refers to the ratio (stated as a percent) of the moisture content of air compared to the saturated moisture level at the same temperature and pressure. Relative humidity can be measured with a hygrometer, in particular with a probe hygrometer from VWR® International.

Herein "min" means "minute" or "minutes". Herein "mol" means mole. Herein "g" following a number means "gram" or "grams". "Ex." means "example". All amounts as they pertain to listed ingredients are based on the active level ("solids") and do not include carriers or by-products that may be included in commercially available materials.

Herein "Comp. Ex." means comparative example; and "Ex." means example.

Herein, "comprising" means that other steps and other ingredients can be included in addition. The compositions, methods, and uses of the present invention can comprise, consist of, and consist essentially of the elements and limitations described herein, as well as any of the additional or optional ingredients, components, steps, or limitations described herein. Embodiments and aspects described herein may comprise or be combinable with elements, features or components of other embodiments and/or aspects despite not being expressly exemplified in combination, unless an incompatibility is stated.

As used herein, the articles including "a" and "an" when used in a claim, are understood to mean one or more of what is claimed or described.

The terms "include", "includes", and "including", as used herein are meant to be non-limiting.

Where amount ranges are given, these are to be understood as being the total amount of said ingredient in the composition, or where more than one species fall within the scope of the ingredient definition, the total amount of all ingredients fitting that definition, in the composition. The concentrations mentioned for a given ingredient are total concentration ranges in case more than one of the given ingredient is present. The specified ranges are provided by weight and relate to the total weight of the personal cleansing composition, unless specifically stated otherwise.

For example, if the composition comprises from 1% to 5% fatty alcohol, then a composition comprising 2% stearyl alcohol and 1% cetyl alcohol and no other fatty alcohol, would fall within this scope.

The amount of each particular ingredient or mixtures thereof described hereinafter can account for up to 100% (or 100%) of the total amount of the ingredient(s) in the composition.

The term "mixtures" as used herein is meant to include a simple combination of materials and any compounds that may result from their combination.

The term "molecular weight" or "M.Wt." as used herein refers to the weight average molecular weight unless otherwise stated. The weight average molecular weight can be measured by gel permeation chromatography ("GPC").

The term "personal cleansing composition" as used herein refers to compositions intended for topical application to the skin or hair for cleansing. The personal cleansing composition may be aqueous.

The term "isotropic" as used herein refers to a particular phase of the composition wherein the structure is "identical along any three orthogonal directions in space, and is therefore dark or 'nonbirefringent' when viewed between crossed polarized light filters. (One direction is 'orthogonal' to another if the vector component of the first, in the direction of the second, is zero.)" (Laughlin, R. G. (1994). "The Aqueous Phase Behavior of Surfactants," 182, 8.2).

The term "anisotropic" as used herein refers a particular phase of the composition wherein the structure exhibits properties with different values when measured in different directions. An anisotropic phase is not identical along any three orthogonal directions in space, and is birefringent when viewed between crossed polarized light filters.

The term "liquid crystals" as used herein refers to anisotropic fluids or mesophases. Liquid crystals as used herein are polymeric liquid crystals. The polymeric liquid crystalline phase of the personal cleansing composition is lyotrophic meaning that the polymer liquid crystalline phase contains a solvent, namely water. This type of polymer liquid crystals is distinguished in the art from thermotropic, heat, and magnetically induced liquid crystals. The liquid crystalline state exists between the boundaries of the solid crystalline phase and the isotropic liquid phase (i.e. an intermediate between the three dimensionally ordered crystalline state and the disordered dissolved state). In this state, some of the molecular order characteristics of the solid crystalline phase are retained in the liquid state because of the molecular structure and short range intermolecular interaction. Liquid crystals are also known as anisotropic fluids, a fourth state of matter, polymer association structure or mesophases. Those terms are used interchangeably. Lyotropic means a material is formed through changes in solution behavior (and hence by definition contains a solvent, e.g. water) of the ingredients. The changes involve thermal and salvation energies. The term "lyotropic liquid crystal" as used herein, refers to a liquid crystalline phase distinctive by the presence of birefringence under polarized light microscopy.

The term "birefringence" as used herein refers the property of the material to capable of transmitting light when viewed with cross polars under static conditions.

The term "micelle" as used herein refers structure comprising individual surfactant molecules aggregated to form a hydrophobic core region with externally facing polar head groups in equilibrium with surfactant monomers in a polar phase, having a characteristic dimension that is a single digit multiple of the surfactant length, i.e., generally less than about 10 nm in diameter.

The term "rinse-off" as used herein means the intended product usage includes application to skin and/or hair followed by rinsing and/or wiping the product from the skin and/or hair within a few seconds to minutes of the application step. The product is generally applied and rinsed in the same usage event, for example, a shower.

The term "statically stable" as used herein, unless otherwise specified, refers to a personal cleansing composition that comprises at least two compositions that maintain at least two "separate" phases with at least two separate benefit concentration zones contained within a single chamber package at ambient conditions for a period of at least about 180 days. Alternatively, static stability can be determined by accelerated protocol at elevated temperature. One accelerated protocol is based on passing static stability after 10 days at 50° C. By "separate" is meant that there is substantially no mixing of compositions contained in the zones, detected by the benefit analysis method, described hereinafter, prior to dispensing of the composition.

The term "substantially free of" as used herein means less than 1%, less than 0.8%, less than 0.5%, less than 0.3%, or less than an immaterial amount of a stated ingredient by total weight of the composition.

The term "free of" as used herein refers to no detectable amount of the stated ingredient.

The term "surfactant" as used herein refers to amphiphilic molecules which can aggregate to form micelles and other surfactant structures, which are soluble in an aqueous phase and contribute to foaming during a cleansing event, i.e., stabilizing an air interface.

The term "structured" as used herein means having a rheology that confers stability on the personal cleansing composition. The degree of structure is determined by rheologic characteristics such as the yield stress determined by the Herschel-Bulkley Rheology Test Method or the viscosity obtained by the Ultracentrifugation Test Method, all in the Test Method section below.

Thickeners are useful for adjusting the viscosity and the rheological behavior of personal cleansing compositions in order to make them easy to pour and dose. Structurants thicken, but also provide a suspensive benefit, allowing ingredients such as oils, particulates, and the like, to be stably suspended in the personal cleansing composition.

The inventors have surprisingly found that instead of thickening the composition, a natural polysaccharide such as xanthan gum or a chemically modified natural polysaccharide can lead to the formation of a polymer liquid crystalline phase in the personal cleansing composition and even at a relatively low amount from 0.05% to 5% of the natural polysaccharide or a chemically modified natural polysaccharide by total weight of the composition.

The personal cleansing composition comprises a first and second phase. The first phase is an isotropic and micellar surfactant phase. The second phase is a polymer liquid crystalline phase. The first and second phases of the personal cleansing composition may be separated by ultracentrifuge. The polymer liquid crystalline phase is characterized by birefringence. The polymer liquid crystalline phase and the personal cleansing composition may have a specific rheologic profile.

The polymer liquid crystalline phase of the composition provides the structure of the personal cleansing composition. The polymer liquid crystalline phase comprises polymer liquid crystals. The polymer liquid crystals include the natural polysaccharide or the chemically modified natural polysaccharide. The polymer liquid crystalline phase can help the personal cleansing composition to suspend a benefit agent selected from the group consisting of hair care and skin care benefit agents, particulates, particles, like silica and titanium oxide, microcapsules, oils, droplets, pigments or coloring agents, opacifiers, pearlescent agents, feel modifiers, oil absorbers, skin protectants, matting agents, friction enhancers, slip agents, conditioning agents, exfoliants, odor absorbers, or cleaning enhancers, and mixtures thereof.

The personal cleansing composition may have specific yield stress $\tau_y$, as an elastic component of the composition, measured according to the Herschel-Burlley Rheology Test Method.

In order to provide further structure and suspend further benefit agents, the personal cleansing composition may comprise the polymer liquid crystalline phase, and at a sufficient yield stress $\tau_y$ from 0.005 to 3 Pa measured according to the Herschel-Bulkley Rheology Test Method.

Furthermore, for providing a stable personal cleansing composition comprising fatty acyl isethionate surfactant, the personal cleansing composition may also exhibit a flow viscosity from 3 Pa·s to 100 Pa·s at 25° C. at a shear rate of 1.5 $s^{-1}$ according to the Flow Viscosity Test Method.

Hence, it has been found that a stable personal cleansing composition able to suspend benefits agents and comprising fatty acyl isethionate can be provided when the composition comprises a polymer liquid crystalline phase comprising polymer liquid crystals, wherein the polymer liquid crystals include the natural polysaccharide or the chemically modified natural polysaccharide.

Surfactant System

The personal cleansing composition is free of alkyl sulfate and alkyl ether sulfate type of surfactant. In one example, the personal cleansing composition does not comprise any alkyl sulfate which comprises $C_{12}$-$C_{18}$ alkyl sulfate or any alkyl ether sulfate including alkyl glyceryl ether sulfates.

The personal cleansing composition may not comprise any alkyl ether sulfates which are those having the formula:

wherein R is an alkyl or alkenyl having 8 to 18 carbons, or 12 to 18 carbons, n has an average value of greater than at least 0.5, or between 2 and 3; and M is a solubilizing cation such as sodium, potassium, ammonium or substituted ammonium.

The personal cleansing composition may not comprise any ammonium and sodium lauryl ether sulfates.

If the personal cleansing composition does contain alkyl sulfate and/or alkyl ether sulfate type of surfactant, its content of such a weight proportion of: alkyl sulfates or alkyl ether sulfate type surfactant is less than or equal to the sum of 0.6, less than or equal to the sum of 0.2, or equal to 0.

The personal cleansing composition comprises a surfactant system. The surfactant system comprises from 0.1% to 5%, from 0.2% to 4%, from 0.5% to 3.5% of a fatty acyl isethionate surfactant by weight of the composition; and from 0.5% to 40%, from 1% to 25%, from 5% to 15% of a co-surfactant by weight of the composition.

Fatty Acyl Isethionate

The fatty acyl isethionate surfactant may be defined as an isethionate according to the general formula (I):

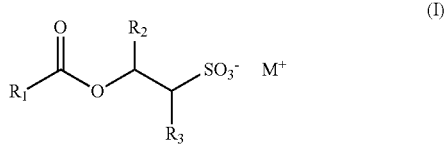

wherein $R_1$ is a saturated or unsaturated, straight or branched, alkyl or alkenyl chain with from 6 to 30 carbon atoms, from 8 to 22 carbon atoms, from 9 to 18 carbon atoms, $R_2$ and $R_3$ are each independently H or ($C_1$-$C_4$) alkyl, and $M^+$ is an alkali metal, like lithium, sodium, potassium; or $M^+$ is an alkali-earth metal, like magnesium; or $M^+$ is an ammonium or a substituted ammonium cation; or wherein $R_1$ is a saturated or unsaturated, straight or branched alkyl or alkenyl, like an alkyl chain with from 6 to 30 carbon atoms, from 8 to 22 carbon atoms, from 9 to 18 carbon atoms, $R_2$ and $R_3$ are H, and $M^+$ is an alkali metal, like sodium, potassium; or $M^+$ is an ammonium cation; or wherein $R_1$ is a saturated or unsaturated, straight or branched alkyl chain with from 9 to 18 carbon atoms, $R_2$ and $R_3$ are H, and $M^+$ is sodium or an ammonium cation.

Suitable fatty acyl isethionate surfactants may include the reaction product of fatty acids esterified with isethionic acid and neutralized with sodium hydroxide. Suitable fatty acids for isethionate surfactants can be derived from coconut oil or palm kernel oil, for instance. Additional examples of suitable isethionic anionic surfactants are described in U.S. Pat. Nos. 2,486,921; 2,486,922; and 2,396,278, each of which is incorporated herein by reference.

The fatty acyl isethionate surfactant may be selected from the group consisting of sodium lauroyl isethionate, sodium lauroyl methyl isethionate, sodium oleoyl isethionate, sodium oleoyl methyl isethionate, sodium stearoyl isethionate, sodium stearoyl methyl isethionate, sodium myristoyl isethionate, sodium myristoyl methyl isethionate, sodium palmitoyl isethionate, sodium palmitoyl methyl isethionate, sodium cocoyl isethionate, sodium cocoyl methyl isethionate, a blend of stearic acid and sodium cocoyl isethionate, ammonium cocoyl isethionate, ammonium cocoyl methyl isethionate, and mixtures thereof.

The fatty acyl isethionate surfactant may be selected from the group consisting of sodium lauroyl isethionate, sodium myristoyl isethionate, sodium palmitoyl isethionate, sodium stearoyl isethionate, sodium oleoyl isethionate, sodium cocoyl isethionate, ammonium cocoyl isethionate, and mixtures thereof.

The fatty acyl isethionate surfactant may be selected from the group consisting of sodium lauroyl isethionate, sodium cocoyl isethionate, ammonium cocoyl isethionate, and mixtures thereof.

Corresponding commercial products are available, for example, from the company Innospec under the trade name "Iselux®" and from Clariant or Uniquema under the trade names "Hostapon®" or "Arlatone®". Examples of other commercial fatty acyl isethionates that may be used can be Hostapon® surfactants from Clariant such as for sodium cocoyl isethionate: Hostapon® SCI-85C, Hostapon® SCI-78C, or a blend of stearic acid with sodium cocoyl isethionate: Hostapon® SCI-65C. Examples of other commercial fatty acyl isethionates that may be used can be "Jordapon®" surfactants from BASF such as Jordapon® CI prill or Jordapon® CI65; and sodium cocoyl isethionate from Yongan Daily Chemical Co. such as YA-SCI-85® or YA-SCI-65®.

Fatty acyl isethionates surfactants are typically prepared by the reaction of an isethionate salt such as metal or ammonium isethionate and an a saturated or unsaturated, straight or branched, alkyl or alkenyl chain fatty acid having from 6 to 30 carbon atoms, from 8 to 22 carbon atoms, from 6 to 18 carbon atoms. Depending on the processing conditions used, the resulting fatty acyl isethionate surfactant can be a mixture of 45% to 95% by weight of fatty acyl isethionates and 40 to 0 wt % of free fatty acids, in addition to isethionates salts, typically less than 5 wt. %, and trace (less than 2 wt. %) of other impurities, by total weight of the resulting fatty acyl isethionate surfactant. A mixture of aliphatic fatty acids may be used for the preparation of commercial fatty acyl isethionates surfactants.

The personal cleansing composition comprises a surfactant system. The surfactant system comprises from 0.1% to 5%, from 0.2% to 4%, from 0.5% to 3.5% of a fatty acyl isethionate surfactant by weight of the composition. The concentrations mentioned here are total concentration ranges in case more than one fatty acyl isethionate surfactant is present. The specified ranges are provided by weight and relate to the total weight of the personal cleansing composition.

Fatty acyl isethionate surfactants have not typically been used in preparation of personal cleansing compositions because they might readily form solid crystals (when used alone and/or with a co-surfactant) and consequently might make it difficult to form stable liquid personal cleansing compositions.

Co-Surfactant

The surfactant system comprises from 0.5% to 40%, from 1% to 25%, from 5% to 15% of a co-surfactant by weight of the composition. The co-surfactant may be selected from the group consisting of an anionic surfactant being not an isethionate surfactant, a non-ionic surfactant, an amphoteric surfactant, a zwitterionic surfactant and mixtures thereof.

The anionic surfactant of the co-surfactant, being not an isethionate surfactant may be selected from the group consisting of fatty acyl sarcosinates, sulfosuccinates, sulfonates, sulfoacetates, acyl glycinates, acyl alaninates, acyl glutamates, lactates, lactylates, glucose carboxylates, amphoacetates, taurates, and mixtures thereof.

In that case, alkyl is defined as a saturated or unsaturated, straight or branched alkyl chain with 6 to 30 carbon atoms, 8 to 22 carbon atoms, or with 9 to 18 carbon atoms. In that case, acyl is defined as of formula R—C(O)—, wherein R is a saturated or unsaturated, straight or branched alkyl or alkenyl, like an alkyl chain with 6 to 30 carbon atoms, with 8 to 22 carbon atoms, with 9 to 18 carbon atoms.

The fatty acyl sarcosinate may be a sarcosinate according to the general formula (II):

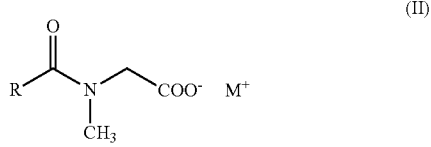

(II)

wherein R is a saturated or unsaturated, straight or branched alkyl or alkenyl, like an alkyl chain with 7 to 17 carbon atoms, with 9 to 13 carbon atoms and $M^+$ is H, a sodium, potassium or ammonium cation.

Non-limiting examples of sarcosinates may be selected from the group consisting of sodium lauroyl sarcosinate, sodium cocoyl sarcosinate, sodium myristoyl sarcosinate, TEA-cocoyl sarcosinate, ammonium cocoyl sarcosinate, ammonium lauroyl sarcosinate, dimer dilinoleyl bis-lauroyl glutamate/lauroyl sarcosinate, disodium lauroamphodiacetate, lauroyl sarcosinate, isopropyl lauroyl sarcosinate, potassium cocoyl sarcosinate, potassium lauroyl sarcosinate, sodium cocoyl sarcosinate, sodium lauroyl sarcosinate, sodium myristoyl sarcosinate, sodium oleoyl sarcosinate, sodium palmitoyl sarcosinate, TEA-cocoyl sarcosinate, TEA-lauroyl sarcosinate, TEA-oleoyl sarcosinate, TEA-palm kernel sarcosinate, and mixtures thereof.

The fatty acyl sarcosinate may be selected from the group consisting of sodium lauroyl sarcosinate, sodium myristoyl sarcosinate, sodium cocoyl sarcosinate, and mixtures thereof.

Non-limiting examples of sulfosuccinate surfactants can include disodium N-octadecyl sulfosuccinate, disodium lauryl sulfosuccinate, diammonium lauryl sulfosuccinate, sodium lauryl sulfosuccinate, disodium laureth sulfosuccinate, tetrasodium N-(1,2-dicarboxyethyl)-N-octadecyl sulfosuccinnate, diamyl ester of sodium sulfosuccinic acid, dihexyl ester of sodium sulfosuccinic acid, dioctyl esters of sodium sulfosuccinic acid, and combinations thereof.

Non-limiting examples of sulfonates can include alpha olefin sulfonates, linear alkylbenzene sulfonates, sodium laurylglucosides hydroxypropylsulfonate, and combinations thereof.

Non-limiting examples of sulfoacetates can include sodium lauryl sulfoacetate, ammonium lauryl sulfoacetate, and combination thereof.

Non-limiting examples of acyl glycinates can include sodium cocoyl glycinate, sodium lauroyl glycinate, and combination thereof.

Non-limiting example of acyl alaninates can include sodium cocoyl alaninate, sodium lauroyl alaninate, sodium N-dodecanoyl-1-alaninate, and combinations thereof.

Non-limiting examples of acyl glutamates can be selected from the group consisting of sodium cocoyl glutamate, disodium cocoyl glutamate, ammonium cocoyl glutamate, diammonium cocoyl glutamate, sodium lauroyl glutamate, disodium lauroyl glutamate, sodium cocoyl hydrolyzed wheat protein glutamate, disodium cocoyl hydrolyzed wheat protein glutamate, potassium cocoyl glutamate, dipotassium cocoyl glutamate, potassium lauroyl glutamate, dipotassium lauroyl glutamate, potassium cocoyl hydrolyzed wheat protein glutamate, dipotassium cocoyl hydrolyzed wheat protein glutamate, sodium capryloyl glutamate, disodium capryloyl glutamate, potassium capryloyl glutamate, dipotassium capryloyl glutamate, sodium undecylenoyl glutamate, disodium undecylenoyl glutamate, potassium undecylenoyl glutamate, dipotassium undecylenoyl glutamate, disodium hydrogenated tallow glutamate, sodium stearoyl glutamate, disodium stearoyl glutamate, potassium stearoyl glutamate, dipotassium stearoyl glutamate, sodium myristoyl glutamate, disodium myristoyl glutamate, potassium myristoyl glutamate, dipotassium myristoyl glutamate, sodium cocoyl/hydrogenated tallow glutamate, sodium cocoyl/palmoyl/sunfloweroyl glutamate, sodium hydrogenated tallowoyl glutamate, sodium olivoyl glutamate, disodium olivoyl glutamate, sodium palmoyl glutamate, disodium palmoyl glutamate, TEA-cocoyl glutamate, TEA-hydrogenated tallowoyl glutamate, TEA-lauroyl glutamate, and mixtures thereof.

Non-limiting example of lactates can include sodium lactate.

Non-limiting examples of lactylates can include sodium lauroyl lactylate, sodium cocoyl lactylate, and combination thereof.

Non-limiting examples of glucose carboxylates can include sodium lauryl glucoside carboxylate, sodium cocoyl glucoside carboxylate, and combinations thereof.

Non-limiting examples of alkylamphoacetates can include sodium cocoyl amphoacetate, sodium lauroyl amphoacetate, and combination thereof.

Non-limiting examples of acyl taurates can include sodium methyl cocoyl taurate, sodium methyl lauroyl taurate, sodium methyl oleoyl taurate, and combinations thereof.

Alternatively, the anionic surfactants of the co-surfactant may be selected from the group consisting of sodium tridecyl benzene sulfonate, sodium dodecyl benzene sulfonate, sodium lauroyl sarcosinate, sodium lauroyl sarcosinate, sodium cocoyl sarcosinate, sodium lauroyl glycinate, sodium cocoyl glycinate, potassium lauroyl glycinate, potassium cocoyl glycinate, sodium lauroyl glutamate, potassium lauroyl glutamate, sodium cocoyl glutamate, potassium cocoyl glutamate, disodium lauroyl glutamate, dipotassium lauroyl glutamate, disodium cocoyl glutamate, dipotassium cocoyl glutamate, sodium lauroyl lactylate, and mixtures thereof.

The surfactant system may comprise from 0.5% to 15%, from 1% to 10%, from 2% to 5% of an anionic surfactant of the co-surfactant, being not an isethionate surfactant, a fatty acyl sarcosinate, by total weight of the composition.

The non-ionic surfactant of the co-surfactant may be selected from the group consisting of glucosides, alkyl amines, alcohol ethoxylates, alkyl polyglucosides, alkyl glucosides, acyl glutamide, and mixtures thereof.

The surfactant system may comprise from 1% to 10% of a non-ionic surfactant, from 3% to 9% of a non-ionic surfactant, from 5% to 9% of a non-ionic surfactant by total weight of the composition.

The non-ionic surfactants may be selected from the group consisting of cocoamide monoethanolamine, lauramide monoethanolamine, cocoyl glucoside, lauroyl glucoside, decyl glucoside, and mixtures thereof.

The co-surfactant of the personal cleansing composition may include an amphoteric surfactant or a zwitterionic surfactant. Suitable amphoteric or zwitterionic surfactants can include those described in U.S. Pat. Nos. 5,104,646 and 5,106,609.

Amphoteric surfactants can include those that can be broadly described as derivatives of aliphatic secondary and tertiary amines in which an aliphatic radical can be straight or branched chain and wherein an aliphatic substituent can contain from 8 to 18 carbon atoms such that one carbon atom can contain an anionic water solubilizing group, e.g., carboxy, sulfonate, sulfate, phosphate, or phosphonate. Examples of compounds falling within this definition can be sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and products described in U.S. Pat. No. 2,528,378.

The amphoteric surfactant included in the personal cleansing composition described herein may be selected from the group consisting of sodium lauroamphoacetate, sodium cocoamphoacetate, disodium lauroamphoacetate, disodium cocodiamphoacetate, and mixtures thereof.

Zwitterionic surfactants suitable for use in the co-surfactants of the personal cleansing composition described herein may include those that are broadly described as derivatives of aliphatic quaternary ammonium, phosphonium, and sulfonium compounds, in which the aliphatic radicals can be straight or branched chains, and wherein one of the aliphatic substituents can contain from 8 to 18 carbon atoms and one can contain an anionic group, e.g., carboxy, sulfonate, sulfate, phosphate, or phosphonate.

The zwitterionic surfactant included in the personal cleansing composition described herein may include one or more betaines, including cocoamidopropyl betaine.

Alternatively, the amphoteric or zwitterionic surfactant may be selected from cocoamidopropyl betaine, lauramidopropyl betaine, coco-betaine, lauryl betaine, cocoamphoacetate, cocoamphodiacetate, lauroamphoacetate, lauroamphodiacetate, lauramine oxide, and mixtures thereof.

The surfactant system may further comprise a zwitterionic surfactant selected from the group consisting of: lauryl hydroxysultaine, cocamidopropyl hydroxysultaine, coco-betaine, coco-hydroxysultaine, coco-sultaine, lauryl betaine, lauryl sultaine, and mixtures thereof.

Examples of betaine zwitterionic surfactants may include coco dimethyl carboxymethyl betaine, cocoamidopropyl betaine (CAPB), coco-betaine, lauryl amidopropyl betaine (LAPB), oleyl betaine, lauryl dimethyl carboxymethyl betaine, lauryl dimethyl alpha-carboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, and mixtures thereof. Examples of sulfobetaines may include coco dimethyl sulfopropyl betaine, stearyl dimethyl sulfopropyl betaine, lauryl dimethyl sulfoethyl betaine, lauryl bis-(2-hydroxyethyl) sulfopropyl betaine and mixtures thereof.

The zwitterionic surfactant can comprise or consist of cocamidopropyl betaine (CAPB), lauramidopropyl betaine (LAPB), and combinations thereof.

The zwitterionic surfactant of the co-surfacant may be a betaine, like a betaine selected from the group consisting of cocamidopropyl betaine, lauramidopropyl betaine, coco betaine, lauryl betaine, coco hydroxysultaine and mixtures thereof; or cocamidopropyl betaine.

The co-surfactant may comprise at least a combination of a fatty acyl sarcosinate and a betaine; like a fatty acyl sarcosinate selected from the group consisting of sodium lauroyl sarcosinate, sodium myristoyl sarcosinate, sodium cocoyl sarcosinate, and mixtures thereof, and a betaine selected from the group consisting of coco hydroxysultaine, lauryl hydroxysultaine, coco betaine, and mixtures thereof; or sodium lauroyl sarcosinate and cocamidopropyl betaine.

The personal cleansing composition may comprise a total amount from 0.6% to 55% of the surfactant system by total weight of the composition, from 5% to 50% of the surfactant system by total weight of the composition, from 10% to 45% of the surfactant system by total weight of the composition. The concentrations mentioned here are total concentration ranges of the surfactant system resulting from at least the addition of the total concentration ranges of the fatty acyl isethionate surfactant and the co-surfactant. The specified ranges are provided by weight and relate to the total weight of the personal cleansing composition.

Natural Polysaccharide

The personal cleansing composition comprises from 0.05% to 5%, from 0.1% to 4%, from 0.25% to 2% of a natural polysaccharide or a chemically modified natural polysaccharide by weight of the composition.

Polysaccharides are composed of many monosaccharide residues that are joined one to the other by O-glycosidic linkages. Polysaccharides are also called hydrocolloids or gums.

The natural polysaccharide may be selected from the group consisting of cellulose, hemicellulose; pectin; an exudate polysaccharide gum; a mucilage polysaccharide gum; fructan; a seaweed polysaccharide; a microbial polysaccharide; an animal polysaccharide; and mixtures thereof.

The natural polysaccharide may be selected from the group consisting of cellulose, hemicellulose, like D-xylans, arabinoxylans, D-mannans, D-galactomannans, β-D-glucans, D-xyloglucans, D-glucomannans, D-galactans, or arabinogalactans; pectin, like linear homogalacturonan, substituted xylogalacturonan, rhamnogalacturonan type rhamnogalacturonan type I or arabinan; exudate polysaccharide gum, like gum arabic, gum tragacanth, gum karaya or gum ghatti; mucilage polysaccharide gum, like yellow mustard mucilage gum, flaxseed mucilage gum, okra mucilage gum or psyllium gum; fructan, like inulin or levan; seaweed polysaccharide, like alginate, carrageenan, or agar; a microbial polysaccharide, like xanthan gum, pullulan gum or gellan gum; an animal polysaccharide, like chitin or chitosan; and mixtures thereof.

The natural polysaccharide may be cellulose. Cellulose is the major structural polysaccharide in the cell walls of higher plants. Cellulose is a high molecular weight polymer of (1→4)-linked β-D-glucopyranose residues (FIG. 1A—repeating units of cellulose).

Alternatively, the natural polysaccharide may be a hemicellulose selected from the group consisting of D-xylans, arabinoxylans, D-mannans, D-galactomannans, β-D-glucans, D-xyloglucans, D-glucomannans, D-galactans, arabinogalactans, and combinations thereof.

Hemicelluloses are a heterogeneous group of polysaccharides constituting the cell walls of higher plants; these polysaccharides are often physically entangled, covalently and/or noncovalently bonded to cellulose and lignins. The structure of hemicelluloses may vary depending on their origin, but they can be divided into four groups based on composition of their main backbone chain: D-xylans with $(1\rightarrow4)$-linked $\beta$-D-xylose; D-mannans, with $(1\rightarrow4)$-linked $\beta$-D-mannose; D-xyloglucans with D-xylopyranose residues attached to the cellulose chain; and D-galactans with $(1\rightarrow3)$-linked $\beta$-D-galactose.

D-Mannans, found in tagua palm seeds, have a backbone composed of linear $(1\rightarrow4)$-linked $\beta$-D-mannose chains.

The natural polysaccharide may be a D-galactomannan selected from the group consisting of locust bean gum, *senna* gum, guar gum, fenugreek gum, tara gum, and combinations thereof.

Figure 1C:
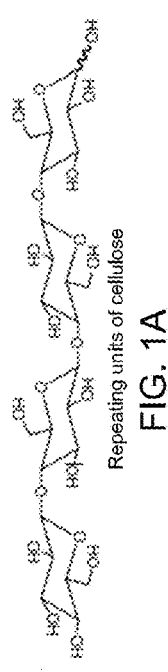
FIG. 1C is related to the structure of methylcellulose.
Figure 1B:
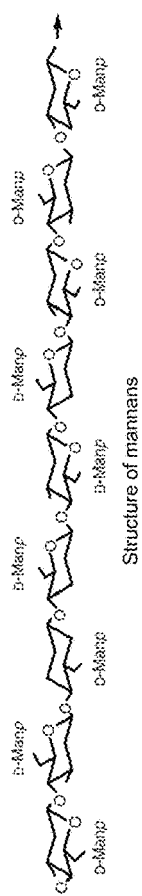
FIG. 1B is related to the structure of carboxymethylcellulose.
Figure 1D:
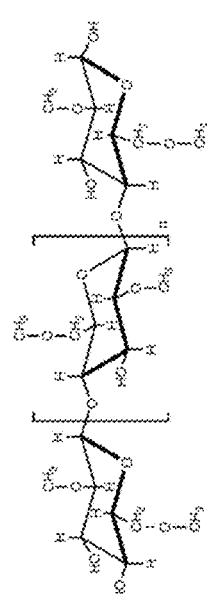
FIG. 1D is related to the structures of mannans and galactomannans.

D-galactomannans have the same linear mannan backbone but they are substituted with $\alpha$-D-Galp side units linked to 0-6 (See FIG. 1D).

Figure 1E:
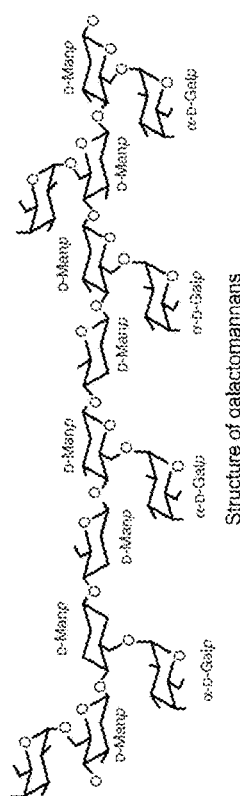
FIG. 1E is related to the structure of xyloglucans.
Figure 1E:
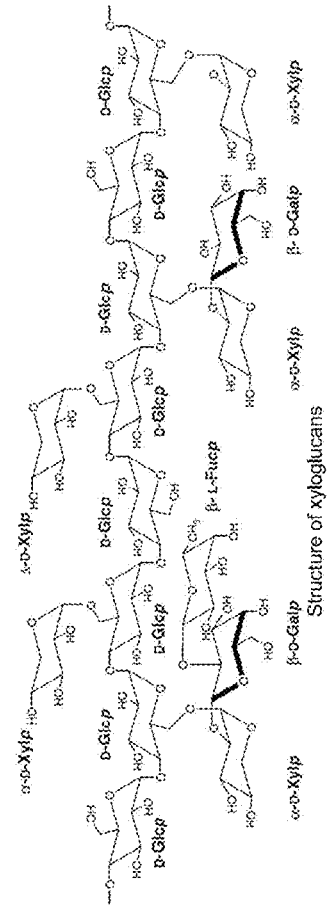

D-Xyloglucans, like cellulose, have linear backbones of $(1\rightarrow4)$-linked $\beta$-D-glucopyranoses (see FIG. 1E).

D-Glucomannans are linear polymers of both $(1\rightarrow4)$-linked $\beta$-D-mannose and $(1-4)$-linked $\beta$-D-glucose residues.

Figure 1F:
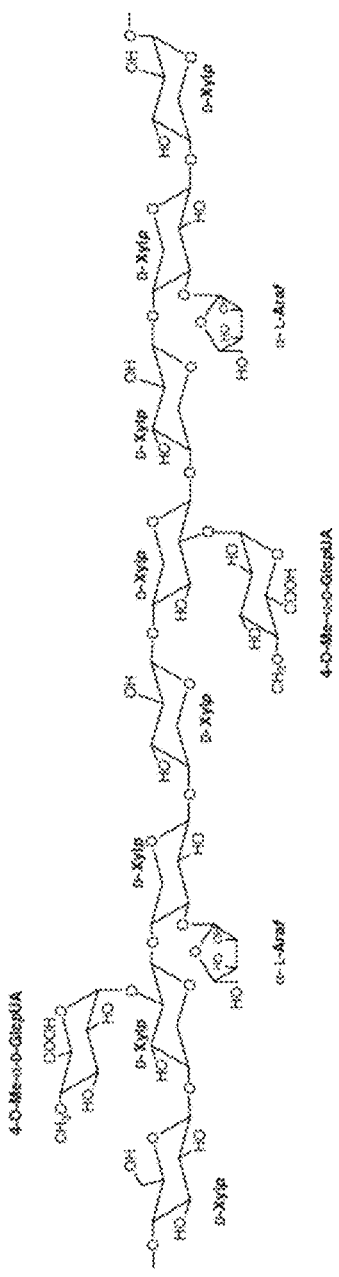
FIG. 1F is related to the structure of arabinoxylans.

Arabinoxylans are composed of $(1\rightarrow4)$-linked $\beta$-D-xylopyranoses with various kinds of side branches, the most common being 4-O-methyl-D-glucopyranosyluronic acid linked mostly to O-2 of $\beta$-Xylp units and $\alpha$-L-Araf linked to 0-3 of $\beta$-Xylp units (FIG. 1F).

Figure 1H:
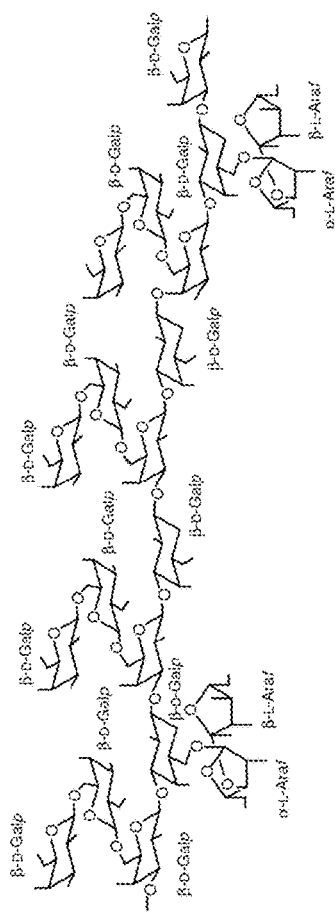
FIG. 1H is related to the structure of arabinogalactans.
Figure 1G:
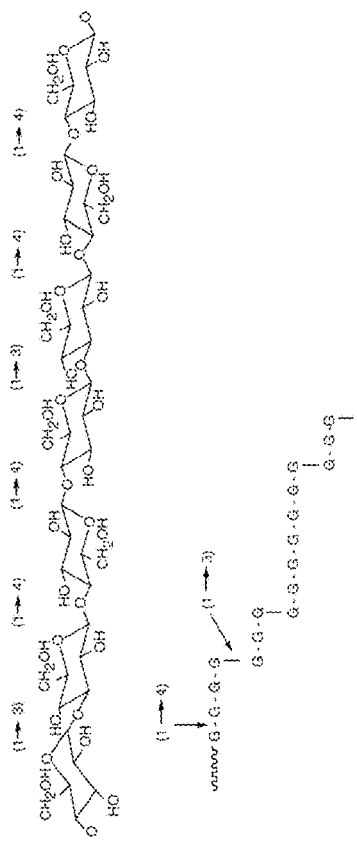
FIG. 1G is related to the structure of mixed linkage (1→3)(1→4) β-D-glucans.

Mixed linkage $(1\rightarrow3)$, $(1\rightarrow4)$ $\beta$-D-glucans are present in the grass species, cereals, and in some lichens (e.g., *Cetraria islandica*) (FIG. 1G).

Arabinogalactan is a major D-galactan obtained from soft-woods such as pine, larch, cedar, and spruce. This polymer has a main backbone of $(1\rightarrow3)$-linked $\beta$-D-galactopyranosyl residues with $\beta$-$(1\rightarrow6)$-linked disaccharides of $\beta$-D-Galp-$(1\rightarrow6)$-$\beta$-D-Galp and $\alpha$-$(1\rightarrow6)$-linked disaccharides of $\beta$-L-Araf-$(1\rightarrow3)$-$\alpha$-L-Araf (FIG. 1H).

Alternatively, the natural polysaccharide may be a pectin selected from the group consisting of linear homogalacturonan, substituted xylogalacturonan, rhamnogalacturonan type II, rhamnogalacturonan type I, arabinan, and combinations thereof.

Pectins are the major components of most higher plant cell walls. Pectins are the most complex class of plant cell wall polysaccharides. They comprise of two families of covalently linked polymers, galacturonans and rhamnogalacturonans (type I).

Galacturonans are segments of pectins with $(1\rightarrow4)$-linked $\alpha$-D-galactosyluronic acid residues in the backbone, such as those in the linear homogalacturonans, in the substituted xylogalacturonans and in rhamnogalacturonans type II (RG II).

Xylogalacturonans have xylopyranosyl residues $\alpha$-$(1\rightarrow3)$-linked to part of the galactosyluronic acid residues in the galacturonan backbone.

The rhamnogalacturonans type II have a homogalacturonan backbone with very complex side chains with respect to sugar residue content and linkage structure. The side chains contain rhamnose and some rare residues, such as apiose, aceric acid (3-C-carboxy-5-deoxy-L-xylose), KDO (3-deoxy-D-manno-octulosic acid), and DHA (3-deoxy-D-lyxo-heptulosaric acid).

Rhamnogalacturonans type I (RG I) have a backbone composed of alternating $(1\rightarrow2)$-linked $\alpha$-L rhamnosyl and $(1\rightarrow4)$-linked $\alpha$-D-galacturonic acid residues.

Arabinans are branched polysaccharides with $(1\rightarrow5)$-linked $\alpha$-L-arabinofuranosyl units constituting the backbone.

Alternatively, the natural polysaccharide may be an exudate gum selected from the group consisting of gum arabic, gum tragacanth, gum karaya, gum ghatti, and combinations thereof. Exudate gums are polysaccharides produced by plants as a result of stress, including physical injury and/or fungal attack.

Alternatively, the natural polysaccharide may be a mucilage gum selected from the group consisting of yellow mustard mucilage gum, flaxseed mucilage gum, okra mucilage gum, psyllium gum, and combinations thereof. Mucilage gums are very viscous polysaccharides extracted from seeds or soft stems of plants; examples are okra mucilage (from *Hibiscus esculentus*), psyllium (from *Plantago* species), yellow mustard (from *Sinapis alba*), and flax mucilage (from *Linum usitatissimum*).

Alternatively, the natural polysaccharide may be a fructan selected from the group consisting of inulin, levan, and combination thereof. Fructans are reserve polysaccharides in certain plants, either complementing or replacing starch. The two main kinds of fructans are inulin and levan. Inulin is a low molecular weight polysaccharide containing $(2\rightarrow1)$ linked $\beta$-D-Frup residues (FIG. 1I). Inulin has a D-glucopyranose nonreducing end unit linked to the O-2 position of the $\beta$-D-Frup residues. Levans are found mainly in grasses. Levans contain a backbone of $(2\rightarrow6)$ linked $\beta$-D-Frup residues with $(2\rightarrow1)$ linked branches of one to four D-frupyranosyl units (FIG. 1J).

Alternatively, the natural polysaccharide may be a seaweed polysaccharide selected from the group consisting of alginate, carrageenan, agar, and combinations thereof.

Alginates constitute the primary structural polysaccharides of brown seaweeds (Phaeophyceae). Alginates are unbranched copolymers of $(1\rightarrow4)$-linked $\beta$-D-mannuronic acid (M) and $\alpha$-L-guluronic acid (G) residues (see FIG. 1K).

The natural polysaccharide may be a carrageenan selected from the group consisting of $\kappa$-carrageenan, $\iota$-carrageenan, $\lambda$-carrageenan, furcellarans, and combinations thereof. The natural polysaccharide may be a carrageenan selected from the group consisting of $\kappa$-carrageenan, $\iota$-carrageenan, $\lambda$-carrageenan, and combinations thereof. The natural polysaccharide may be $\iota$-carrageenan. Alternatively, the natural polysaccharide may be a combination of xanthan gum and $\iota$-carrageenan.

Carrageenans are structural polysaccharides of marine red algae of the Rhodophyceae class. $\kappa$-Carrageenans, $\iota$-carrageenans, and furcellarans are linear polysaccharides whose backbone structure is based on a repeating disaccharide sequence of sulphate esters of $(1\rightarrow3)$ linked $\beta$-D-galactose and $(1\rightarrow4)$ linked 3,6-anhydro-$\alpha$-D-galactose. They differ from each other in the number and position of sulphate groups. $\lambda$-Carrageenan comprise $\beta$-D-galactopyranosyl residue sulphated at C-2 (instead of C-4 as in $\iota$- and $\kappa$-carrageenans) and 2,6-di-O-sulfato-$\alpha$-D-galactopyranosyl units (instead of 3,6-anhydro-$\alpha$-D-galactopyranosyl residue) (See FIG. 1L).

Agar is, therefore, a linear polysaccharide built up of the repeating disaccharide unit of $(1\rightarrow3)$-linked $\beta$-D-galactose and $(1\rightarrow4)$-linked 3,6-anhydro-$\alpha$-L-galactose residues.

Alternatively, the natural polysaccharide may be a microbial polysaccharide selected from the group consisting of xanthan gum, pullulan gum, gellan gum, and combinations thereof.

Figures 1L, 1M:
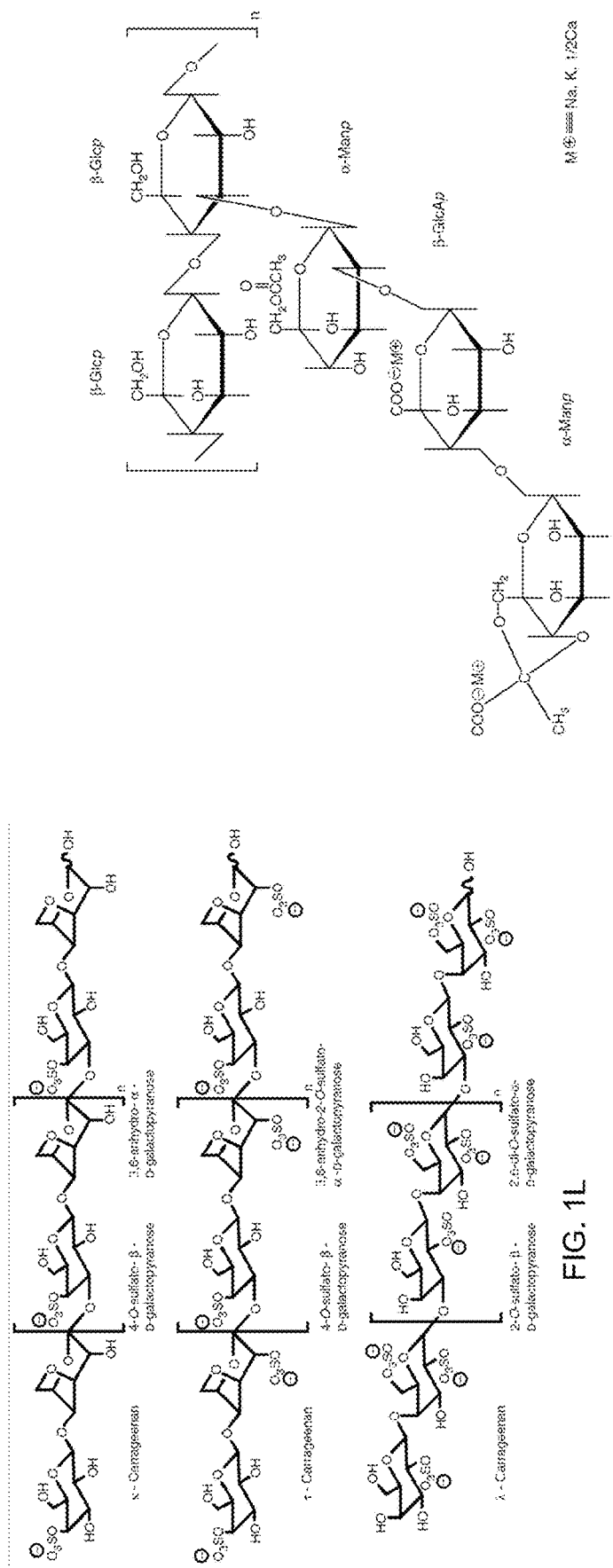
FIG. 1L is related to the structures of κ-carrageenan, ι-carrageenan and λ-carrageenan.
FIG. 1M is related to the structure of xanthan gum.

The natural polysaccharide may be xanthan gum. Xanthan gum is an extracellular polysaccharide produced by the bacterium *Xanthomonas campestris*. The primary structure of xanthan gum consists of the cellulose-like backbone of (1→4)-linked β-DGlcp residues substituted, at O-3 of alternate glucose residues, with a trisaccharide. The trisaccharide consists of the β-D-Manp-(1→4)-β-D-GlcpA-(1→2)-α-D-Manp-(1→unit (FIG. 1M).

Figure 1N:
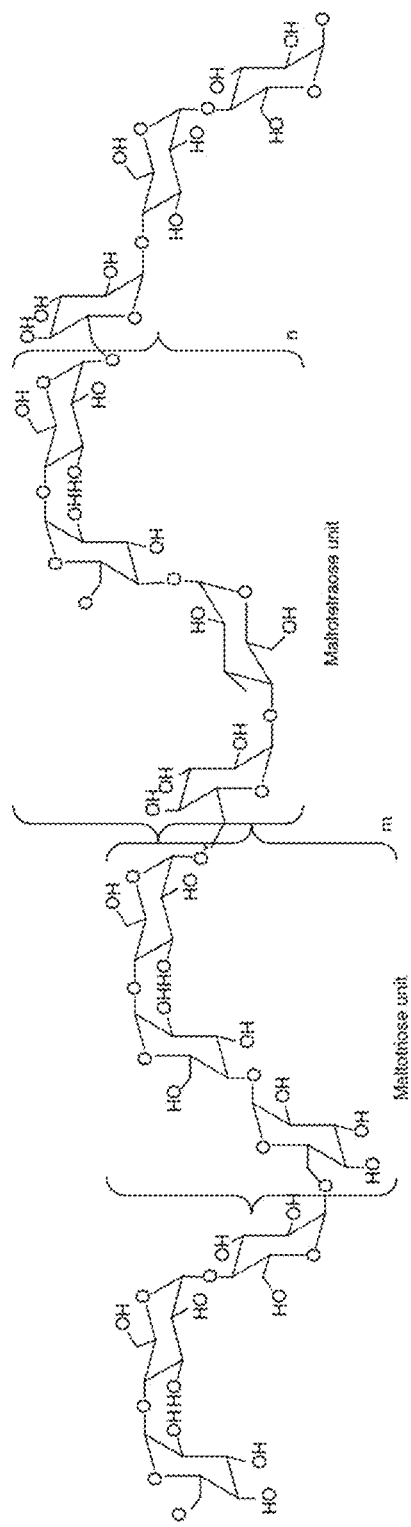
FIG. 1N is related to the structure of pullulan.

Pullulan is an extracellular homopolysaccharide of glucose produced by many species of the fungus *Aureobasidium*, specifically *A. pullulans*. Pullulan contains (1→4) and (1→6)-linked α-D-glucopyranosyl residues. The ratio of (1→4) to (1→6) linkages is 2:1 (See FIG. 1N).

Gellan gum is a deacetylated form of the extracellular bacterial polysaccharide from *Auromonas elodea*. Gellan gum has a repeating tetrasaccharide sequence of →3)-β-D-Glcp-(1→4)-β-D-GlcpA-(1→4)-β-D-Glcp-(1→4)-α-L-Rhap-(1→. Other suitable gellan gums can include native gellan, wellan, S-657 and Rhamsan.

Figure 1O:
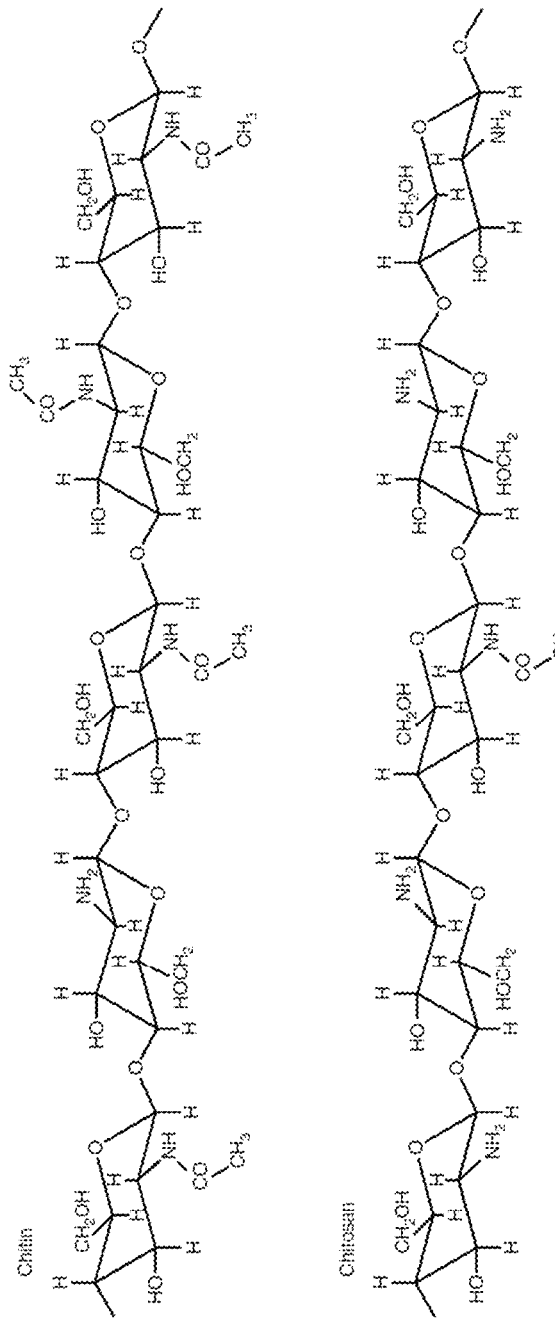
FIG. 1O is related to the structures of chitin and chitosan.

Alternatively, the natural polysaccharide may be an animal polysaccharide selected from the group consisting of chitin, chitosan, and combination thereof. The molecular structure of chitin is similar to that of cellulose, except that the hydroxyl groups at O-2 of the β-D-Glcp residues are substituted with N-acetylamino groups (see FIG. 1O). Chitosan is soluble in acidic aqueous media to give a unique polycationic structure. Chitosan can form a thermo-irreversible gel by chemical and enzymatic reactions. Chitosan gel can also be prepared by introducing large organic counter ions, such as 1-naphthol-4-sulphonic acid or 1-naphthylamine-4-sulphonic acid.

The natural polysaccharide or the chemically modified natural polysaccharide may be selected from the group consisting of xanthan gum, locust bean gum, guar gum, tragacanth gum, carrageenan gum, cellulose gum, hydroxypropylmethylcellulose, xanthan gum/locust bean gum, xanthan gum/guar gum, and mixtures thereof.

The natural polysaccharide may be selected from the group consisting of xanthan gum, κ-carrageenan, ι-carrageenan, λ-carrageenan, xanthan gum/locust bean gum and xanthan gum/guar gum.

The natural polysaccharide may be selected from the group consisting of xanthan gum, ι-carrageenan, xanthan gum/locust bean gum and xanthan gum/guar gum.

Alternatively, the natural polysaccharide may be a glucomannan such as locust bean gum and guar gum that is combined with xanthan gum and/or carrageenans such as κ-carrageenan, ι-carrageenan and λ-carrageenan. Such natural polysaccharide combination can have synergism and provide improved polymer liquid crystals, with an improved yield stress.

The chemically modified natural polysaccharide may be selected from the group consisting of microcrystalline cellulose, carboxymethylcellulose, methylcellulose, hydroxypropylmethylcellulose, hydroxyethylcellulose, hydroxypropylcellulose, and combinations thereof.

Microcrystalline cellulose is prepared by treating natural cellulose with hydrochloric acid to partially dissolve and remove the less organized amorphous regions of this polysaccharide.

Carboxymethylcellulose is an anionic, water-soluble polymer capable of forming very viscous solutions. Carboxymethylcellulose is prepared by first treating cellulose with alkali (alkali cellulose), and then by reacting with monochloroacetic acid. The structure of carboxymethylcellulose is depicted in FIG. 1B.

Methylcellulose is a nonionic cellulose ether (see FIG. 1C). Methylcellulose is prepared by treating alkali cellulose with methyl chloride. Other methylcellulose derivatives are also available, of which hydroxypropylmethylcellulose and hydroxyethylcellulose.

The chemically modified natural polysaccharide may be hydroxypropyl methylcellulose having a viscosity selected from the group consisting of 3,500-5,500 cP, 60,000-90,000 cP, and 60,000-90,000 cP. Indeed, hydroxypropyl methylcellulose may come in a variety of viscosities from, for example, 3,500-5,500 cP (like DOW METHOCEL 40-0202); 60,000-90,000 cP (like DOW METHOCEL 40-0101); and 10,000-16,500 cP (like DOW METHOCEL 40-0100). Information on the viscosities of these materials, etc. can be found on DOW's website www.dow.com.

The chemically modified natural polysaccharide may be hydroxypropyl methylcellulose having a viscosity 60,000-90,000 cP with hydroxypropyl methylcellulose having a viscosity 2,600-5,000 cP, or with xanthan gum.

The chemically modified natural polysaccharide may be hydroxypropyl methylcellulose having a viscosity 60,000-90,000 cP with hydroxypropyl methylcellulose having a viscosity 2,600-5,000 cP in a weight ratio of 75:25.

The chemically modified natural polysaccharide may be hydroxypropyl methylcellulose having a viscosity 60,000-90,000 cP with xanthan gum in a weight ratio of 50:50.

Other natural polysaccharides or chemically modified natural polysaccharides may be used in combination with higher viscosity hydroxypropyl methyl cellulose (3,500-5,000 cP range). These can include lower viscosity hydroxypropyl methyl cellulose with a viscosity of 2,600-5,000 cP (like DOW METHOCEL E4M PRM) or xanthan gum.

The personal cleansing composition may comprise a natural polysaccharide and a chemically modified natural polysaccharide. It is understood that any chemically modified natural polysaccharide disclosed hereinbefore may be combined with any natural polysaccharide disclosed herein before.

Isotropic and Micellar Phase

The personal cleansing composition comprises a first and second phase, as identified and isolated by the Ultracentrifuge Test Method. The first phase of the personal cleansing composition is an isotropic and micellar surfactant phase. The rheologic profile of the first phase has been determined by the Ultracentrifuge Test Method.

The first phase may exhibit a viscosity greater than 1 Pa·s at 25° C. at a shear rate of 1 $s^{-1}$ according to the Ultracentrifuge Test Method. The first phase having a viscosity greater than 1 Pa·s at 25° C. at a shear rate of 1 $s^{-1}$ according to the Ultracentrifuge Test Method can fit the well-known Carreau viscosity profile. A Carreau viscosity profile is typical of a micellar phase. The micellar phase can find its origin from the surfactant system comprising a fatty acyl isethionate surfactant and a co-surfactant.

Furthermore, the first phase cannot rotate polarized light and cannot exhibit a birefringent optical morphology. Also, when isolated according to the Ultracentrifuge test, the first phase has a transmittance at 25° C. and at 640 nm of 100% according to the Optical Clarity Test Method.

The personal cleansing composition may further comprise from 0.05 to 5%, from 0.1% to 4%, or from 0.5% to 3% of an electrolyte by weight of the composition. The addition of an electrolyte can help to elongate the micelles of the surfactant system in the first phase of the personal cleansing composition and to improve the flow viscosity.

The electrolyte may be selected from the group of sodium or potassium citrate, calcium chloride, calcium bromide, zinc chloride, barium chloride, calcium nitrate, potassium chloride, sodium chloride, potassium iodide, sodium bromide, ammonium bromide, sodium sulfate, and mixtures thereof.

The electrolyte may be selected from the group of sodium or potassium citrate, calcium chloride, potassium chloride, sodium chloride, and mixtures thereof.

Polymer Liquid Crystalline Phase

The second phase of the personal cleansing composition is a polymer liquid crystalline phase. The second phase exhibits a birefringent optical morphology indicative of the polymer liquid crystalline phase. The polymer liquid crystalline phase comprises polymer liquid crystals. The polymer liquid crystals include the natural polysaccharide or the chemically modified natural polysaccharide.

As detailed in the example section below, without a natural polysaccharide, e.g. xanthan gum or a chemically modified natural polysaccharide in the personal cleansing composition, no second phase comprising polymer liquid crystals can be observed. In that case, there is no measurable yield stress $\tau_y$, as measured according to the Herschel-Bulkley Rheology Test Method. When adding increasing amount of the natural polysaccharide or a chemically modified natural polysaccharide, a second phase appears. A polymer liquid crystalline phase can be formed. The formation of the second phase being a polymer liquid crystalline phase can be characterized in different ways.

Generally, water-soluble polysaccharide are polymers that are used in predominantly aqueous compositions to provide a rheology benefit due to their solubility. Water-soluble polysaccharides, in solution, absorb substantial amounts of water and increase viscosity of a composition as a result of their size and entanglements. In some cases, the polysaccharides can form gels due to molecular association. A relatively poor water-soluble polysaccharide or a polysaccharide that does not form readily a molecular gel in a composition cannot help to improve the performance of the composition. Indeed, a relatively poor water-soluble polysaccharide is generally quite dense and therefore tends to phase separate and become unstable in a composition.

Polymer liquid crystalline phases are uncommon in personal cleansing compositions, since polymers generally favor disordered structures, especially at low concentration. Polymer polydispersity rules out liquid crystalline structures common to small molecules, i.e., smectic liquid crystalline phases such as lamellar and hexagonal. Nematic and/or cholesteric polymer liquid crystalline structures are known for some polysaccharides, however only at relatively high polysaccharide concentrations, i.e., at least from 10 wt %, at least from 20 wt % of the polysaccharide by total weight of the composition.

Inventors have surprisingly found that a natural polysaccharide or a chemically modified natural polysaccharide can lead to the formation of a polymer liquid crystalline phase at a relatively low concentration of the said polysaccharide, and even in the presence of a surfactant system as described hereinbefore.

Indeed, a natural polysaccharide or a chemically modified natural polysaccharide can lead to the formation of a polymer liquid crystalline phase, at a level from 0.05% to 5%, from 0.1% to 4%, or from 0.25% to 2% of a natural polysaccharide or a chemically modified natural polysaccharide by weight of the composition.

First, the second phase being a polymer liquid crystalline phase provides a structure for the personal cleansing compositions. Such structure is characterized by specific structural features. The second phase of the personal cleansing composition is a polymer liquid crystalline phase. Indeed, the second phase exhibits a birefringent optical morphology indicative of the polymer liquid crystalline phase. The polymer liquid crystalline phase comprises polymer liquid crystals. The polymer liquid crystals include the natural polysaccharide or the chemically modified natural polysaccharide.

The second phase exhibits a birefringent optical morphology indicative of the polymer liquid crystalline phase. The polymer liquid crystalline phase comprises polymer liquid crystals. Microscopic observations indicate that the polymer liquid crystals form elongated structures, and thus have relatively high degrees of orientational order. The polymer liquid crystals may form elongated structures, namely elongated colloidal structures. The polymer liquid crystals may be nematic or cholesteric.

When the polymer liquid crystals are of nematic subclass, the centers of gravity of the polymer liquid crystals are arranged at random, consequently no positional long-range order exists. Within volume elements of a macroscopic sample of the polymer liquid crystalline phase, the axes of all polymer liquid crystals are oriented in a specific direction.

When the polymer liquid crystals are of cholesteric subclass, the arrangement of the polymer liquid crystals are similar to the ones of nematic subclass, however only an orientational order exists in the cholesteric subclass. In contrast to the nematic subclass, the cholesteric subclass is characterized by the fact that the direction of the long axes of the molecules changes continuously within the sample. This leads to a twist about an axis perpendicular to the long axes of the molecules. If the pitch of the helical structure agrees with the wavelength of the visible light, selective reflection of monochromatic light can be observed. This effect may lead to the iridescent colors often observed in cholesteric phases.

The natural polysaccharide or the chemically modified natural polysaccharide may be present in the polymer liquid crystalline phase at a level from 1% to 30%, from 2% to 25%, or from 4% to 10.5% by total weight of the polymer liquid crystalline phase.

The polymer liquid crystals of the second phase may comprise at least a combination of the natural polysaccharide or the chemically modified natural polysaccharide and one ingredient of the surfactant system.

The polymer liquid crystals of the second phase may comprise at least a combination of the natural polysaccharide selected from the group consisting of xanthan gum, ι-carrageenan, xanthan gum/locust bean gum and xanthan gum/guar gum; and the fatty acyl isethionate surfactant.

The polymer liquid crystals of the second phase may comprise at least a combination of xanthan gum a fatty acyl isethionate surfactant; and optionally a co-surfactant.

Surprisingly, it has been found that a natural polysaccharide or a chemically modified natural polysaccharide in an aqueous personal cleansing composition comprising a surfactant system can form a polymer liquid crystalline phase. Further, the polymer liquid crystalline phase can form elongated structures which are very efficient at forming an associative network, conferring a structure. The elongated structures, forming the associative network, can be further characterized by a measurable yield stress, and at surprisingly a relatively low level of the natural polysaccharide or the chemically modified natural polysaccharide. The associative network, may form a relatively weak gel or a physical gel.

The polymer liquid crystals of the polymer liquid crystalline phase may be notably soluble during use. Consumer products such as body wash and shampoo are used with water. The polymer liquid crystals can dissolve during use with additional water, which increases the viscosity of the dilute aqueous micelles of the personal cleansing composition, resulting in a lather improvement. For example, the increased dilute micelle viscosity can form a lather that is relatively denser and creamier. Those attributes may be desirable for a personal cleansing composition.

Also, the personal cleansing composition may exhibit a yield stress value $\tau_y$ from 0.005 Pa to 3 Pa, from 0.02 Pa to 2 Pa, from 0.03 Pa to 1 Pa, or from 0.05 Pa to 0.8 Pa according to the Herschel-Bulkley Rheology Test Method as disclosed herein.

The yield stress of the personal cleansing composition may be a further evidence of the presence of the polymer liquid crystalline phase. The yield stress of the personal cleansing composition can be defined as the elastic component characterizing the necessary structure of the composition to be highly effective at suspending any benefit agents, particulates, particles such as silica and titanium oxide, microcapsules, oils, droplets, and mixtures thereof in the personal cleansing composition. In other words, a polymer liquid crystalline phase and the yield stress value $\tau_y$ as set out above are the features responsible to provide a personal cleansing composition highly effective at suspending particulates, particles such as silica and titanium oxide, microcapsules, oils, droplets, and mixtures thereof. In other words, the polymer liquid crystalline phase and optionally the yield stress value $\tau_y$ as set out above are the features that can help to improve the distribution of benefit agents associated with the personal cleansing composition: skin or hair care ingredients, perfumes, . . . .

The personal cleansing composition may also exhibit a flow viscosity from 3 Pa·s to 100 Pa·s at 25° C. at a shear rate of 1.5 s$^{-1}$ according to the Flow Viscosity Test Method as disclosed herein. The structure provided by the polymer liquid crystalline phase may also characterized by yield stress and the flow viscosity of the composition, imparting a relatively high stability for the personal cleansing composition.

Another further evidence of the polymer liquid crystalline phase may be the transmittance of the personal cleansing composition. The personal cleansing composition may exhibit a transmittance at 25° C. and at 640 nm of from 4% to 95%, from 10% to 93%, or from 25% to 90% according to the Optical Clarity Test Method as disclosed herein. As further detailed below in the example section, the personal cleansing composition without a natural polysaccharide or a chemically modified natural polysaccharide forms typically micelles having relatively high transmittance and typical micelle rheology. However, when adding increasing amount of a natural polysaccharide or a chemically modified natural polysaccharide, the transmittance of the composition decreases. The decrease of transmittance is due to the formation of a second phase which is a polymer liquid crystalline phase.

Optional Ingredients

As can be appreciated, the compositions described herein may include a variety of optional components to tailor the properties and characteristics of the composition. As can be appreciated, suitable optional components are well known and can generally include any components which are physically and chemically compatible with the essential components of the compositions described herein. Optional components should not otherwise unduly impair product stability, aesthetics, or performance. Individual concentrations of optional components can generally range from 0.001% to 10%, by weight of the composition. Optional components can be further limited to components which will not impair the clarity of a translucent composition.

Optional components may include, but are not limited to, conditioning agents (including hydrocarbon oils, fatty esters, silicones), cationic polymers, anti-dandruff actives, and chelating agents. Additional suitable optional ingredients include but are not limited to encapsulated and non-encapsulated perfumes or fragrances, colorants, particles, anti-microbials, foam boosters, anti-static agents, moisturizing agents, propellants, self-foaming agents, pH adjusting agents and buffers, preservatives, pearlescent agents, opacifiers, sensates, suspending agents, solvents, diluents, antioxidants, vitamins and combinations thereof.

Such optional ingredients should be physically and chemically compatible with the components of the composition, and should not otherwise unduly impair product stability, aesthetics, or performance. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein.

Method

The personal cleansing composition may be prepared according to the following method. The method for making the personal cleansing composition as set out hereinbefore may be provided and comprises:

(a) providing a surfactant system, wherein the surfactant system comprises:

from 0.1% to 5%, from 0.2% to 4%, from 0.5% to 3.5% of a fatty acyl isethionate surfactant by weight of the composition;

from 0.5% to 40%, or from 1% to 25%, or from 5% to 15%, of a co-surfactant, wherein the co-surfactant is selected from the group consisting of an anionic surfactant being not an isethionate surfactant, a non-ionic surfactant, an amphoteric surfactant, a zwitterionic surfactant and mixtures thereof, by weight of the composition;

(b) adding from 0.05% to 5%, from 0.1% to 4%, or from 0.25% to 2% of a natural polysaccharide or a chemically modified natural polysaccharide, by weight of the composition with no milling.

As shown in the example section below, when a relatively high energy milling is used for the addition of the natural polysaccharide, the yield stress $\tau_y$ that may characterize the formation of second polymer liquid crystalline phase cannot be met. The step of adding the natural polysaccharide or the chemically modified natural polysaccharide can also impact the orientation of the polymer liquid crystals of the second phase from non-elongated structures that are irregularly shaped with some regularly shaped such as generally spherical domains, to elongated structures.

The natural polysaccharide or the chemically modified natural polysaccharide can be added at the relatively low level from 0.05% to 5%, from 0.1% to 4%, or from 0.25% to 2% of the natural polysaccharide or the chemically modified natural polysaccharide, by weight of the composition with no milling. An increased of the shear when adding the polysaccharide may impede the organization of the second phase into elongated colloidal structures leading to the polymer liquid crystalline phase. The elongated colloidal structures forming the polymer liquid crystals may be characterized by the rheological properties.

The natural polysaccharide or the chemically modified natural polysaccharide may be added to the surfactant system from an aqueous solution comprising from 2% to 30%, from 3% to 20%, or from 4% to 10% of the natural polysaccharide or the chemically modified natural polysaccharide by weight of the aqueous solution.

The natural polysaccharide or the chemically modified natural polysaccharide may be added to the surfactant system by diluting the natural polysaccharide or the chemically modified natural polysaccharide in water at a dilution level from 2% to 30%, from 3% to 20%, or from 4% to 10%. A dilution level of 2% means 2 g of the natural polysaccharide or the chemically modified natural polysaccharide diluted in 100 g of water.

The personal cleansing composition as set out hereinbefore may be obtained by the method for making the personal cleansing composition comprising:
(a) providing a surfactant system, wherein the surfactant system comprises:
from 0.1% to 5%, from 0.2% to 4%, or from 0.5% to 3.5% of a fatty acyl isethionate surfactant by weight of the composition;
from 0.5% to 40%, from 1% to 25%, or from 5% to 15%, of a co-surfactant, wherein the co-surfactant is selected from the group consisting of an anionic surfactant being not an isethionate surfactant, a non-ionic surfactant, an amphoteric surfactant, a zwitterionic surfactant and mixtures thereof, by weight of the composition;
(b) adding from 0.05% to 5%, from 0.1% to 4%, or from 0.25% to 2% of a natural polysaccharide or a chemically modified natural polysaccharide, by weight of the composition with no milling.

Forms and Uses
Product Form

The personal cleansing composition may be presented in typical personal cleansing formulations. They may be in the form of solutions, dispersion, emulsions, foams, and other delivery mechanisms.

The personal cleansing composition may be extrudable or dispensable from a single chamber package. The personal cleansing compositions can be in the form of liquid, semi-liquid, cream, lotion or gel, or solid compositions intended for topical application to skin or hair.

Examples of personal cleansing compositions can include but are not limited to shampoo, conditioning shampoo, hair conditioner, body wash, moisturizing body wash, foaming body wash, shower gels, a shower or bath cream, skin cleansers, cleansing milks, hair and body wash, in shower body moisturizer, gel, emulsion, oil, mousse or spray.

The product forms contemplated for purposes of defining the personal cleansing compositions and methods are rinse-off formulations by which it is meant that the product is applied topically to the skin or hair and then subsequently (i.e., within minutes) rinsed away with water, or otherwise wiped off using a substrate or other suitable removal means.

Uses

The personal cleansing composition as set out hereinabove may be used for improving the lather of the composition.

The personal cleansing composition as set out hereinabove may be used for suspending benefits agents selected from the group consisting of hair care and skin care benefit agents, particulates, particles, like silica and titanium oxide, microcapsules, oils, droplets, pigments or coloring agents, opacifiers, pearlescent agents, feel modifiers, oil absorbers, skin protectants, matting agents, friction enhancers, slip agents, conditioning agents, exfoliants, odor absorbers, or cleaning enhancers, and mixtures thereof.

The personal cleansing composition can advantageously provide relatively improved ecotoxic or ecologically friendly environmental profile.

The personal cleansing composition can help to provide good esthetic properties such as good foam, and is thick and creamy in texture, is silky to the touch and affords conditioning.

Test Methods

It is understood that the Test Methods that are disclosed in the Test Methods Section of the present application can be used to determine the respective values of the parameters as described and claimed herein.

Optical Clarity

The optical clarity of a personal cleansing composition is based on the measurement of the transmittance or light transmission (% T) of the personal cleansing composition at the visible wavelength of light of 640 nm. The transmittance of a personal cleansing composition is measured using a spectrophotometer such as a Thermo Fisher model Genesys 10 VIS (Thermo Fisher Inc, USA) and conventional polystyrene cuvettes with 1 cm path length at 25° C. The spectrophotometer is set to measure the transmittance (% T) at 640 nm wavelength. An identical cuvette filled with distilled water is used as the baseline reference. The personal cleansing composition is pipetted into the cuvette and ensured clear of air bubbles by centrifuging to remove air bubbles if present. The personal cleansing composition in the cuvette is placed in the holder compartment of the instrument, closing the compartment door, and the transmittance (% T) is recorded. In case the personal cleansing composition optionally comprises a dye, or a colored pigment, the baseline reference will be adjusted accordingly.

Flow Viscosity Test Method and Herschel-Bulkley Rheology Test Method

The flow viscosity and the yield stress properties of the personal cleansing composition via the Herschel Bulkley model are measured using a rheometer (available from. TA Instruments of New Castle, Del. AR-G2 series) in a flow mode. The measurements are conducted using a cone and plate geometry measuring system, having a diameter of 40 mm and degree cone angle. The measurement commences after about 10 seconds equilibration time at 25° C. If the composition is substantially structured, i.e. having a flow viscosity greater than 30 000 mPa·s or a yield stress greater than 1 Pa, a cross-hatched parallel plate geometry is used.

The Herschel Bulkley model is described in "Rheometry of Pastes Suspensions and Granular Material" page 163, Philippe Coussot, John Wiley & Sons, Inc., Hoboken, New Jersey. (2005). The flow viscosity and the yield stress value $\tau_y$ of a personal cleansing composition are measured using a 2-step measurement procedure. The yield stress can be obtained using a reverse rate curve from $1\ s^{-1}$ to $10^{-5}\ s^{-1}$ applied over a 6-minute interval, and applying the Herschel-Bulkley model: $\tau = \tau_y + K\gamma^n$, using the data analysis software where $\tau$ is the shear stress, $\tau_y$ is the yield stress, $\gamma$ is the shear rate, K is the viscosity and n is a power law viscosity coefficient.

The rheometer procedure applied herein comprises the step of:

In step 1, the rheometer is set up and operated following standard procedures that include zeroing the gap, bearing friction calibration, and mapping. The geometry can be altered as needed to accommodate relatively high or low viscosity personal cleansing compositions, including selecting a parallel plate geometry for compositions containing particles and serrated geometries for compositions that can exhibit wall slip. Viscosity measurements are conducted at 25° C.

Load the personal cleansing composition onto the rheometer baseplate, ensuring there are no bubbles or gaps, lower the geometry to 100 μm above measurement position, lock the geometry and trim the sample. Lower the gap to the measurement position and place a protective wind shield around the measurement area. Conduct a first shear rate continuous ramp. Start at 1.0 $s^{-1}$ and reduce the shear rate logarithmically to $10^{-5}$ $s^{-1}$ over a 6-minute interval collecting 15 points per rate decade change.

Immediately following, in a step 2, increase the shear rate from 0.025 $s^{-1}$ to 250 $s^{-1}$ over 4 minutes, collecting 15 points per rate decade. Fit the results from the first step to the Herschel-Bulkley rheology model to determine the yield stress of the composition, fitting only the data at and below 0.01 $s^{-1}$ shear rate. Determine the flow viscosity of the composition using the data from the step 2 at 1.5 $s^{-1}$.

Optical Microscopy Test Method

The light microscopy of liquid crystals is described in the Microscopy of Liquid Crystals, Norman Hartshorne, Microscopy publications, Ltd., Chicago, Illinois, U.S.A., 1974. Methods for microscopic observation and evaluation are discussed in Chapter 1, p. 1-20, and ion Chapter 6, p. 79-90. A preferred method for determining occurrence of polymer liquid crystals is by observing birefringence from relatively thin slices of the personal cleansing composition under a polarizing microscope.

The characterization of the second phase of the personal cleansing composition in terms of birefringence, type of structures and orientation of the polymer liquid crystals can be thus viewed using an optical microscope such as a Zeiss Zxio Imager or its equivalent. A drop of the personal cleansing composition is loaded onto a clean glass slide and thinned using a coverslip. Views of the personal cleansing composition using 5×, 10× and 20× objective lenses using bright field can determine the presence of discrete structures of a second phase. Under the cross polarized light optical microscope, one can rotate into view a polarizer and analyzer in cross-polarized position to determine if the second phase is ordered (transmits light) or isotropic (dark). An ordered second phase may characterize a polymer liquid crystalline phase.

If the second phase appears to contain structures that are generally longer than they are wide, including structures that are cylindrical, rod-like, ribbon-like, needle-like or fiber-like in appearance, the second phase is said to contain elongated structures.

The structure of the second phase of the personal cleansing composition is evaluated with a sufficient number of fields by selecting a composition sample from different parts of the total composition (e.g. different parts of the composition contained in a container). At least 5 drops of the personal cleansing composition are used to prepare 5 microscope slides to obtain an average representation of the personal cleansing composition.

Ultracentrifuge Test Method

The weight percentage of the first and second phases of the personal cleansing composition can be determined with the Ultracentrifuge Test using a Beckman Coulter Optima LE-80K ultracentrifuge with swinging bucket rotors (Beckman SW06Ti with 6 buckets, rotor diameter 165 mm, or equivalent).

The tare weight of an ultracentrifuge tube is determined using a 3-place electronic balance to the closest milligram. The ultracentrifuge tube is filled with the personal cleansing composition and the gross weight is measured. The personal cleansing composition in the ultracentrifuge tube is placed in the ultracentrifuge bucket, capped, and placed on the ultracentrifuge rotor. The process is continued with other compositions placed on the rotor in counterbalancing positions. The rotor is positioned in the ultracentrifuge, the vacuum door closed, and run at a speed of 50,000 rpm, at 25° C. for 15 hrs under vacuum. Then, the ultracentrifuge tubes are removed and observed.

A first phase which is an optically transparent micellar surfactant phase is present in the personal cleansing compositions as a layer which is generally a top layer in the ultracentrifuge tube. The micellar surfactant phase has a viscosity which is measured by removing a portion of the first phase using a pipette, transferring it to a rheometer, and measuring the viscosity using the Flow Viscosity Test Method. The micelle viscosity as measured in step 2 of the Flow viscosity Test Method is reported as the Micelle Viscosity, in Pa·s. The entire micellar surfactant phase is carefully removed using a spatula and absorbent means such as paper towels without disturbing lower phases. Weigh the ultracentrifuge tube with the lower phase, subtracting the ultracentrifuge tube tare weight to obtain the relative amounts of the removed micellar and remaining phases. Continue to remove lower phase individually and weighing the ultracentrifuge tube to obtain the weight of each phase. The second phase which can be a birefringent phase, is a polymer liquid crystal phase. The second phase is generally simple to identify based on its structure and appearance.

Express the percentage of each phase, including the polymer liquid crystal phase as a percentage by weight of the total composition, excluding the weight of the ultracentrifuge tube.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

The following examples were prepared:

| | Compositions (wt. %) | | | | | |
|---|---|---|---|---|---|---|
| Ingredients | Comp. Ex. 1 | Ex. 1 | Ex. 2 | Ex. 3 | Ex. 4 | Ex. 5 |
| Sodium cocoyl isethionate[1] | 4.22 | 4.22 | 4.14 | 4.22 | 4.22 | 4.22 |
| Coamidopropyl betaine[2] | 11.03 | 11.03 | 10.82 | 11.03 | 11.03 | 11.02 |
| Sodium lauroyl sarcosinate[3] | 4.75 | 4.75 | 4.66 | 4.75 | 4.75 | 4.75 |
| Sodium chloride[4] | 4.22 | 4.22 | 4.14 | 4.22 | 4.22 | 4.22 |

-continued

| Compositions (wt. %) | | | | | | |
|---|---|---|---|---|---|---|
| Xanthan gum[5] | — | 0.06 | 0.10 | 0.25 | 0.50 | 1.00 |
| Preservative | 0.85 | 0.85 | 0.85 | 0.85 | 0.85 | 0.85 |
| Fragrance | 0.80 | 0.80 | 0.80 | 0.80 | 0.80 | 0.80 |
| water | qs | qs | qs | qs | qs | qs |
| Mixing process | vortexer | vortexer | vortexer | vortexer | vortexer | vortexer |
| Gum addition procedure | A | A | A | A | A | A |
| Total surfactant | 20 | 20 | 19.6 | 20 | 20 | 20 |
| Flow viscosity (Pa · s) | 36.55 | 36.39 | 36.04 | 40.20 | 47.02 | 63.80 |
| Yield stress $\tau_y$ (Pa) | 0 | 0.0258 | 0.0404 | 0.0198 | 0.330 | 0.404 |
| Transmittance (% T at 640 nm) | 87% | — | 64% | 38% | 26% | 7% |
| Hold air bubbles 24 hr | No | Yes | Yes | Yes | Yes | Yes |
| Static stability | n.a. | stable | stable | stable | stable | stable |
| % polymer liquid crystals (Ultracentrifuge Test Method) | 0% | — | — | — | 4.5% | — |
| Birefringence of the 2$^{nd}$ phase | No | Yes | Yes | Yes | Yes | Yes |
| Orientation of the 2$^{nd}$ phase | n.a. | E | E | E | E | E |

| Ingredients | Ex. 6 | Ex. 7 | Ex. 8 | Ex. 9 |
|---|---|---|---|---|
| Sodium cocoyl isethionate[1] | 4.22 | 2.11 | 2.11 | 2.11 |
| Coamidopropyl betaine[2] | 11.03 | 5.51 | 5.51 | 5.51 |
| Sodium lauroyl sarcosinate[3] | 4.75 | 2.37 | 2.37 | 2.37 |
| Sodium chloride[4] | 4.22 | 2.11 | 2.11 | 2.11 |
| Xanthan gum[5] | 2.00 | 0.50 | 1.00 | 2.00 |
| Preservative | 0.85 | 0.85 | 0.85 | 0.85 |
| Fragrance | 0.80 | 0.80 | 0.80 | 0.80 |
| water | qs | qs | qs | qs |
| Mixing process | vortexer | vortexer | vortexer | vortexer |
| Gum addition procedure | A | A | A | A |
| Total surfactant | 20 | 10 | 10 | 10 |
| Flow viscosity (Pa · s) | 65.69 | 9.44 | 17.85 | 33.99 |
| Yield stress $\tau_y$ (Pa) | 0.281 | 0.793 | 1.92 | 0.379 |
| Transmittance (% T at 640 nm) | — | 10% | 4% | — |
| Hold air bubbles 24 hr | Yes | Yes | Yes | Yes |
| Static stability | stable | stable | stable | stable |
| % polymer liquid crystals (Ultracentrifuge Test Method) | — | 5.3% | 6.6% | 10.5% |
| Birefringence of the 2$^{nd}$ phase | Yes | Yes | Yes | Yes |
| Orientation of the 2$^{nd}$ phase | E | E | E | E |
| Micelle viscosity - 1$^{st}$ phase (mPa · s) (Ultracentrifuge Test Method) | — | 2.95 | 3.09 | 2.51 |

Definitions of Components
*[1]Sodium cocoyl isethionate; Supplier Clariant
*[2]Cocamidopropyl Betaine; Supplier BASF
*[3]Sodium lauroyl sarcosinate; Supplier Clariant
*[4]Sodium chloride; Supplier Morton International
*[5]Xanthan gum; Supplier CP Kelco
qs: sufficient quantity for 100% wt.
n.a. not applicable
E: elongated structures Results:

Without a natural polysaccharide, e.g. xanthan gum in the composition of Comparative Example 1, no second phase comprising polymer liquid crystals has been observed. In that case, there is no yield stress $\tau_y$ measured according to the Herschel-Bulkley Rheology Test Method. When adding increasing amount of the natural polysaccharide, e.g. xanthan gum, a second phase appears. A polymer liquid crystalline phase is thus formed. The polymer liquid crystalline phase may be observed for Examples 1-6 with 20% wt. of total surfactant by total weight of the composition, and for Examples 7-9 with 10% wt. of total surfactant by total weight of the composition.

The polymer liquid crystalline phase comprises polymer liquid crystals. The presence of polymer liquid crystals can be characterized by the fact that the personal cleansing composition comprises a yield stress $\tau_y$ measured according to the Herschel-Bulkley model. The personal cleansing composition may exhibit a yield stress $\tau_y$ from 0.005 Pa to 3 Pa according to the Herschel-Bulkley Rheology Test Method. When increasing amount of the natural polysaccharide, e.g. xanthan gum, the yield stress $\tau_y$ and the flow viscosity in some extent both increase. The personal cleansing composition is also statically stable.

The polymer liquids crystals are characterized by their birefringence via optical microscopy. Microscopic observations indicate that the polymer liquid crystals form elongated structures, and thus have relatively high degrees of orientational order.

Figure 2:
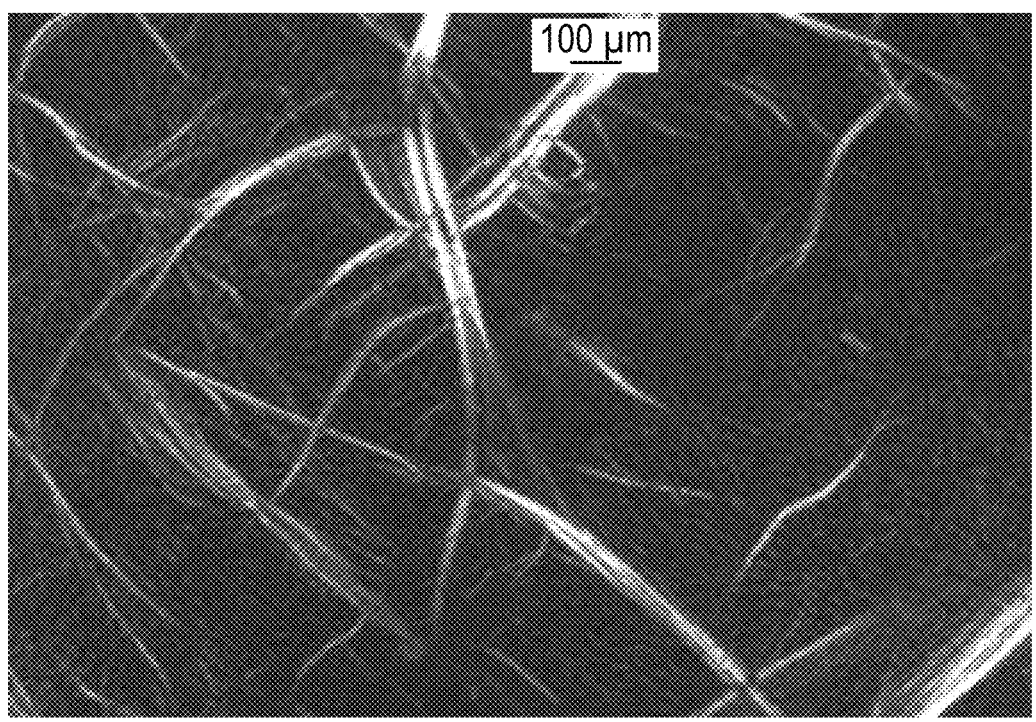
FIG. 2 represents a cross-polarized image of an example according to the present invention taken with a cross-polarized microscopy.

FIG. 2 is a cross-polarized image of Example 5 taken with a cross-polarized light microscopy. The image of FIG. 2 demonstrates a dispersed second phase which is distributed in the form of elongated structures that are optically birefringent. The elongate structures E of the dispersed polymer liquid crystal phase contrast with the first phase being an isotropic and micellar surfactant phase that cannot rotate light and forming the background. The presence of the polymer liquid crystalline phase provides the structural feature of the personal cleansing composition that contributes to the relatively high flow viscosity.

Due to the presence of a polymer liquid crystalline phase conferring a yield stress, the personal cleansing composition can suspend air bubbles. After 24 hours, the presence of air bubbles within a personal cleansing composition is a further evidence of a structure. In other words, the personal cleansing composition is provided with a structure characterized by a polymer liquid crystalline phase and optionally a significant yield stress. Such structure can suspend one or more benefit agents such that hair care or skin care benefits agents, particulates, particles, oils, liquid droplets.

It is also observed a reduction of the transmittance when adding xanthan gum, which demonstrates light scattering due to the polymer liquid crystalline phase. The optical clarity upon addition of a natural polysaccharide, e.g. xanthan gum was assessed for the following base composition (wt. %) in FIG. 3:

| Ingredients | Base composition |
|---|---|
| Sodium cocoyl isethionate[1] | 2.64 |
| Coamidopropyl betaine[2] | 6.89 |
| Sodium lauroyl sarcosinate[3] | 2.97 |
| Sodium chloride[4] | 3.00 |
| Preservative | 0.75 |
| Fragrance | 0.80 |
| water | qs |

Figure 3:
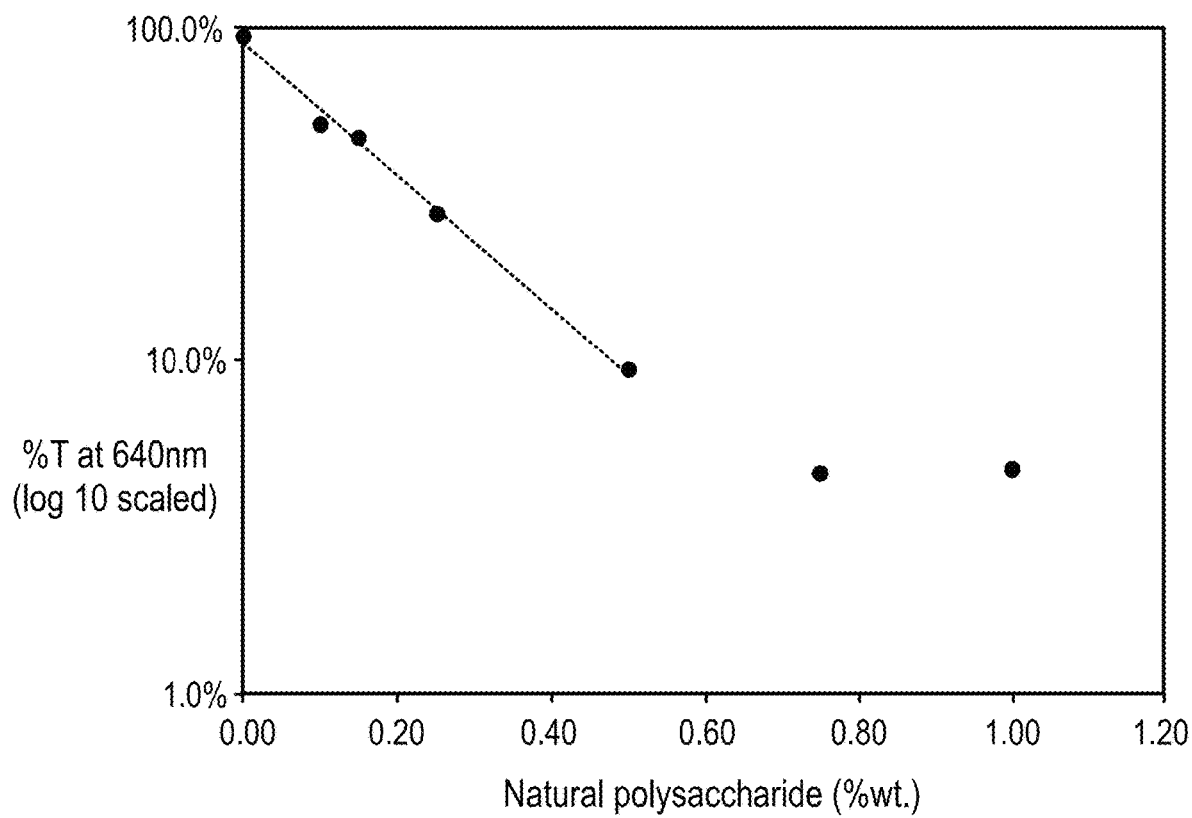
FIG. 3 represents the optical clarity of the personal cleansing composition by plotting the transmittance at 640 nm versus the weight fraction of the natural polysaccharide.

As shown in FIG. 3, the transmittance of the personal cleansing composition is relatively high when no xanthan gum was added to the composition. The personal cleansing composition without xanthan gum forms typically micelles having relatively high transmittance and typical micelle rheology. However, when adding increasing amount of xanthan gum, the transmittance of the composition decreases. The decrease of transmittance is not only due to the insoluble character of xanthan gum in the first phase being an isotropic and micellar surfactant phase, but also due to the formation of a second phase which is a polymer liquid crystalline phase.

For Examples 7-9, at 10% wt. total surfactant by total weight of the composition, a micellar surfactant phase was isolated by the Ultracentrifuge Test Method. Indeed, two distinct phases were observed and separated for Examples 7-9. A top phase comprising a transparent micellar phase was separated from a lower and denser second phase. The second phase rotates polarized light. The measured micelle viscosities for Examples 7-9 show that the micelles of the micellar surfactant phase can contribute to the flow viscosity of the personal cleansing composition.

Furthermore, the polymer liquid crystalline phase that only represents for instance 5.3% wt. of the total composition in Example 7 can effectively triple the micellar viscosity to lead to the flow viscosity of the composition. The relatively denser second phase was observed to sediment, which is also another characteristic of a liquid crystalline phase enriched with the natural polysaccharide and not a surfactant liquid crystal. Surfactant liquid crystals are known to provide creaminess and not to sediment due to their hydrocarbon enrichment.

The following examples were prepared to show that the personal cleansing compositions useful herein needs a sufficient flow viscosity by adjusting either the amount of the natural polysaccharide, or the total surfactant, or the electrolyte.

| | Compositions (wt. %) | | | | |
|---|---|---|---|---|---|
| Ingredients | Comp. Ex. 2 | Comp. Ex. 3 | Comp. Ex. 4 | Ex. 10 | Ex. 11 |
| Sodium cocoyl isethionate[1] | 2.11 | 2.11 | 2.11 | 2.11 | 3.17 |
| Coamidopropyl betaine[2] | 5.51 | 5.51 | 5.51 | 5.51 | 8.27 |
| Sodium lauroyl sarcosinate[3] | 2.37 | 2.37 | 2.37 | 2.37 | 3.56 |
| Sodium chloride[4] | 2.11 | 2.11 | 0 | 2.11 | 3.17 |
| Xanthan gum[5] | — | 0.10 | 0.25 | 0.25 | 0.10 |
| Preservative | 0.85 | 0.85 | 0.75 | 0.85 | 0.75 |
| Fragrance | 0.80 | 0.80 | 0.80 | 0.80 | 0.80 |
| water | qs | qs | qs | qs | qs |
| Mixing process | vortexer | vortexer | vortexer | vortexer | vortexer |
| Gum addition procedure | A | A | A | A | A |
| Total surfactant | 10 | 10 | 10 | 10 | 15 |
| Flow viscosity (Pa · s) | 1.92 | 2.59 | 0.59 | 3.37 | 15.33 |
| Yield stress $\tau_y$ (Pa) | 0 | 0.0125 | 0.0332 | 0.0531 | 0.0531 |
| Static stability | n.a. | separated | separated | stable | stable |
| Birefringence of the $2^{nd}$ phase | No | Yes | Yes | Yes | Yes |
| Orientation of the $2^{nd}$ phase | n.a. | E | E | E | E |

| Ingredients | Ex. 12 | Ex. 13 | Ex. 14 |
|---|---|---|---|
| Sodium cocoyl isethionate[1] | 3.17 | 3.17 | 4.22 |
| Coamidopropyl betaine[2] | 8.27 | 8.27 | 11.03 |
| Sodium lauroyl sarcosinate[3] | 3.56 | 3.56 | 4.75 |
| Sodium chloride[4] | 0 | 0 | 0 |
| Xanthan gum[5] | 0.25 | 0.50 | 0.25 |
| Preservative | 0.75 | 0.75 | 0.75 |
| Fragrance | 0.80 | 0.80 | 0.80 |
| water | qs | qs | qs |
| Mixing process | vortexer | vortexer | vortexer |
| Gum addition procedure | A | A | A |
| Total surfactant | 15 | 15 | 20 |
| Flow viscosity (Pa · s) | 8.46 | 11.16 | 37.43 |

-continued

| Compositions (wt. %) | | | |
|---|---|---|---|
| Yield stress $\tau_y$ (Pa) | 0.0165 | 0.0282 | 0.0507 |
| Static stability | Stable | Stable | Stable |
| Birefringence of the $2^{nd}$ phase | Yes | Yes | Yes |
| Orientation of the $2^{nd}$ phase | E | E | E |

Results:

The personal cleansing compositions useful herein may need a sufficient flow viscosity by adjusting either the amount of the natural polysaccharide, or the total amount of surfactant, optionally with the amount of the electrolyte, e.g. sodium chloride.

Indeed, when the flow viscosity is below 3 Pa·s such as Comparative Example 3 although the yield stress is acceptable, the personal cleansing composition is so unstable that the composition separates in only few days.

Examples 10 and 11 show that sodium chloride can optionally help to increase the flow viscosity. However, Examples 12, 13 and 14 demonstrate that a respective total amount of 15% wt. or 20% wt. of total surfactant by total weight of the composition with the addition of a natural polysaccharide allows reaching a sufficient flow viscosity without adding an electrolyte such as sodium chloride.

The following examples were prepared with different combinations of natural polysaccharides or with other natural polysaccharides:

| Compositions (wt. %) | | | | | |
|---|---|---|---|---|---|
| Ingredients | Ex. 15 | Ex. 16 | Ex. 17 | Ex. 18 | Ex. 19 |
| Sodium cocoyl isethionate[1] | 3.17 | 3.17 | 3.17 | 3.17 | 3.01 |
| Coamidopropyl betaine[2] | 8.27 | 8.27 | 8.27 | 8.27 | 7.86 |
| Sodium lauroyl sarcosinate[3] | 3.56 | 3.56 | 3.56 | 3.56 | 3.38 |
| Sodium chloride[4] | 3.16 | 3.16 | 3.17 | 3.17 | 4.0 |
| Xanthan gum[5] | 0.40 | 0.25 | 0.40 | 0.25 | — |
| Locust bean gum[6] | 0.10 | 0.25 | — | — | — |
| Guar gum[7] | — | — | 0.10 | 0.25 | — |
| ι-carrageenan[8] | — | — | — | — | 3.5 |
| water | qs | qs | qs | qs | qs |
| Mixing process | vortexer | vortexer | vortexer | vortexer | vortexer |
| addition procedure | A | A | A | A | A |
| Total surfactant | 15 | 15 | 15 | 15 | 14.25 |
| Flow viscosity (Pa · s) | 24.52 | 23.86 | 23.16 | 19.85 | 39.00 |
| Yield stress $\tau_y$ (Pa) | 0.224 | 0.222 | 0.156 | 0.0325 | 0.59 |
| Hold air bubble 24 hr | Yes | Yes | Yes | No | Yes |
| Static stability | stable | stable | stable | stable | stable |
| Birefringence of the $2^{nd}$ phase | Yes | Yes | Yes | Yes | Yes |
| Orientation of the $2^{nd}$ phase | E | E | E | E | E |

Definitions of Compoents
*[6]Locust bean gum; Sulpplier (local food distributer)
*[7]guar gum; Supplier Salvay
*[8]ι-carrageenan gum; Supplier CP Kelco The personal cleansing compositions can be prepared using a mixture of natural polysaccharides such as xanthan gum with locust bean gum or xanthan gum with guar gum; or using a carrageenan like ι-carrageenan.

Addition Procedure of the Natural Polysaccharide
Method A:

24 h prior to making the personal cleansing composition, xanthan gum was diluted in water as a level of 5-10% by weight (i.e. 5-10 g of xanthan gum in 100 g of water) as a homogeneous aqueous gel with stirring and via a vortex agitation using a Speedmixer. The xanthan gum preparation was added and stirred into the composition comprising all the other ingredients as the final step and swirled for 5-10 seconds using a vortexer.

The following examples were prepared according to different addition procedures of the natural polysaccharide:

Compositions (wt. %)

| Ingredients | Comp. Ex. 5 | Ex. 20 | Ex. 21 | Ex. 22 |
|---|---|---|---|---|
| Sodium cocoyl isethionate[1] | 3.01 | 3.01 | 3.01 | 3.01 |
| Coamidopropyl betaine[2] | 7.86 | 7.86 | 7.86 | 7.86 |
| Sodium lauroyl sarcosinate[3] | 3.38 | 3.38 | 3.38 | 3.38 |
| Sodium chloride[4] | 3.50 | 4.0 | 4.0 | 4.0 |
| Xanthan gum[5] | 0.25 | 0.25 | 0.50 | 0.50 |
| Preservative | 0.85 | 0.85 | 0.85 | 0.85 |
| Fragrance | 0.80 | 0.80 | 0.80 | 0.80 |
| Silica (agglomerated) | — | — | — | 3.0 |
| water | qs | qs | qs | qs |
| addition procedure | B | C | C | D |
| Total surfactant | 14.25 | 14.25 | 14.25 | 14.25 |
| Total size of the batch | 200 kg | 100 kg | 50 kg | 50 kg |
| Flow viscosity (Pa · s) | 6.49 | 10.95 | 8.67 | 29.77 |
| Yield stress $\tau_y$ (Pa) | 0.0044 | 0.0353 | 0.0205 | 0.242 |
| Hold air bubble 24 hr | No | No | No | Yes |
| Static stability | stable | stable | stable | stable |
| Birefringence of the $2^{nd}$ phase | Yes | Yes | Yes | Yes |
| Orientation of the $2^{nd}$ phase | X | Mostly X with some E | Mostly X with some E | E |

X; the second phase of the personal cleansing composition is distributed as non-elongated structers, which are irregulary shaped or regularly shaped such as generally spherical domains, visible by light microscopy with a 5x-10x objective lens;
E: the second phase pf the personal cleansing composition is distributed primary as elongated structers comprising of generally rod-like structures with high aspect ratio observed by light microscopy. In polarized light microscopy with a 5x-10x objective lens the fibers may generally appear optically birefringent.

X: the second phase of the personal cleansing composition is distributed as non-elongated structures, which are irregularly shaped or regularly shaped such as generally spherical domains, visible by light microscopy with a 5x-10x objective lens;

E: the second phase of the personal cleansing composition is distributed primarily as elongated structures comprising of generally rod-like structures with high aspect ratio observed by light microscopy. In polarized light microscopy with a 5x-10x objective lens the fibers may generally appear optically birefringent.

Addition Procedures of the Natural Polysaccharide
Method B:

The natural polysaccharide, e.g. xanthan gum was added as a dry powder using a Quadro mixer to water, the surfactant system (sodium cocoyl isethionate, cocamidopropyl betaine and sodium lauroyl sarcosinate), followed by the rest of the ingredients of the batch at 70° C., with 6 subsequent theoretical passes following incorporation to provide high energy milling to improve xanthan gum incorporation.

Method C:

The natural polysaccharide, e.g. xanthan gum was added as a dry powder using a pilot plant scale Quadro mixer with no additional milling after incorporation to the batch comprising water, the surfactant system (sodium cocoyl isethionate, cocamidopropyl betaine and sodium lauroyl sarcosinate), followed by the rest of the ingredients.

Method D:

The natural polysaccharide, e.g. xanthan gum was added through a 250 mesh US Standard Sieve onto the moving top surface of the batch comprising the surfactant system (sodium cocoyl isethionate, cocamidopropyl betaine and sodium lauroyl sarcosinate) at 70° C., over several minutes, with no milling or pumping, followed by the rest of the ingredients.

Results:

When a relatively high energy milling is used for the addition of the natural polysaccharide, the yield stress $\tau_y$ that may characterize the formation of second polymer liquid crystalline phase cannot be met. The addition method can also impact the orientation of the polymer liquid crystals of the second phase from non-elongated structures that are irregularly shaped with some regularly shaped such as generally spherical domains, to elongated structures.

Example 21 has a yield stress $\tau_y$ of 0.242 Pa that enables to suspend silica particles without settling. The personal cleansing compositions having a second polymer liquid crystalline phase and a sufficient yield stress $\tau_y$ can help to suspend benefit agents.

Indeed, the polymer liquid crystalline phase can help to provide structuring benefits, in particular the suspension of particles or insoluble liquid droplets throughout the personal cleansing composition without significant settling of such particles or droplets toward the bottom of the container and/or without significant raising or creaming of such particles or droplets toward the top of the container of the composition.

The flow viscosity profiles of different personal cleansing compositions have been generated. For this, the personal cleansing compositions were prepared:

| Ingredients | Compositions (wt. %) | | | | |
| --- | --- | --- | --- | --- | --- |
| | Comp. Ex. 1A | A | B | C | D |
| Sodium cocoyl isethionate[1] | 3.01 | 3.01 | 3.01 | 3.01 | 3.01 |
| Cocamidopropyl betaine[2] | 7.86 | 7.86 | 7.86 | 7.86 | 7.86 |
| Sodium lauroyl sarcosinate[3] | 3.38 | 3.38 | 3.38 | 3.38 | 3.38 |
| Sodium chloride[4] | 3.5 | 3.5 | 3.5 | 3.5 | 3.5 |
| Xanthan gum (dry)[5] | — | 0.10 | 0.25 | — | — |
| Xanthan gum (5% aqueous solution)[5] | — | — | — | 0.10 | 0.25 |
| Preservative | 0.85 | 0.85 | 0.85 | 0.85 | 0.85 |
| Fragrance | 0.80 | 0.80 | 0.80 | 0.80 | 0.80 |
| water | qs | qs | qs | qs | qs |

FIGS. 3A and 3B are related to the flow viscosity profile of personal cleansing compositions comprising xanthan gum added dry or added from a 5% aqueous solution to the composition, respectively upon preparation of the compositions or after 3 days aging at ambient temperature.

Figure 4A:
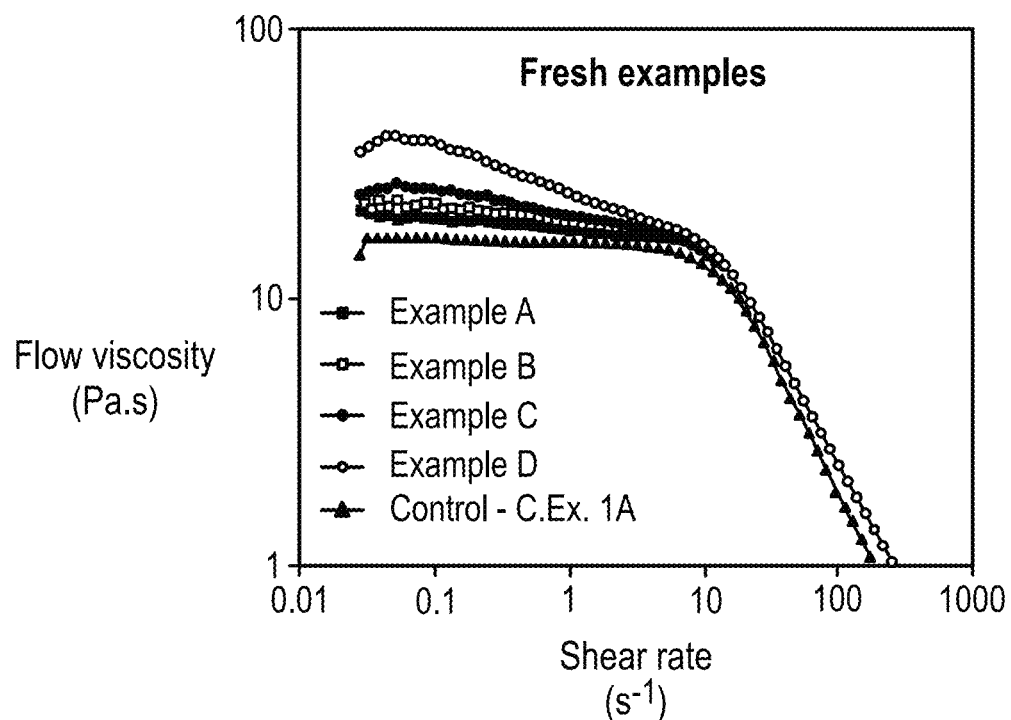
FIGS. 4A and 4B are related to the flow viscosity profile of personal cleansing compositions comprising xanthan gum added dry or added from a 5% aqueous solution to the composition, respectively upon preparation of the compositions or after 3 days aging at ambient temperature.

In FIG. 4A, relative to the control curve without any xanthan gum (Comparative Example 1A), the addition of xanthan gum increases the flow viscosity across the shear rate spectrum despite the known insolubility of xanthan gum.

In FIG. 4A, when xanthan gum is added from a 5% aqueous solution (Examples C and D), a significant enhancement of the flow viscosity is obtained than when xanthan gum is added dry (Examples A and B). It is assumed that the pre-solubilization of the natural polysaccharide polymer can improve the flow viscosity profile of the personal cleansing composition.

Figure 4B:
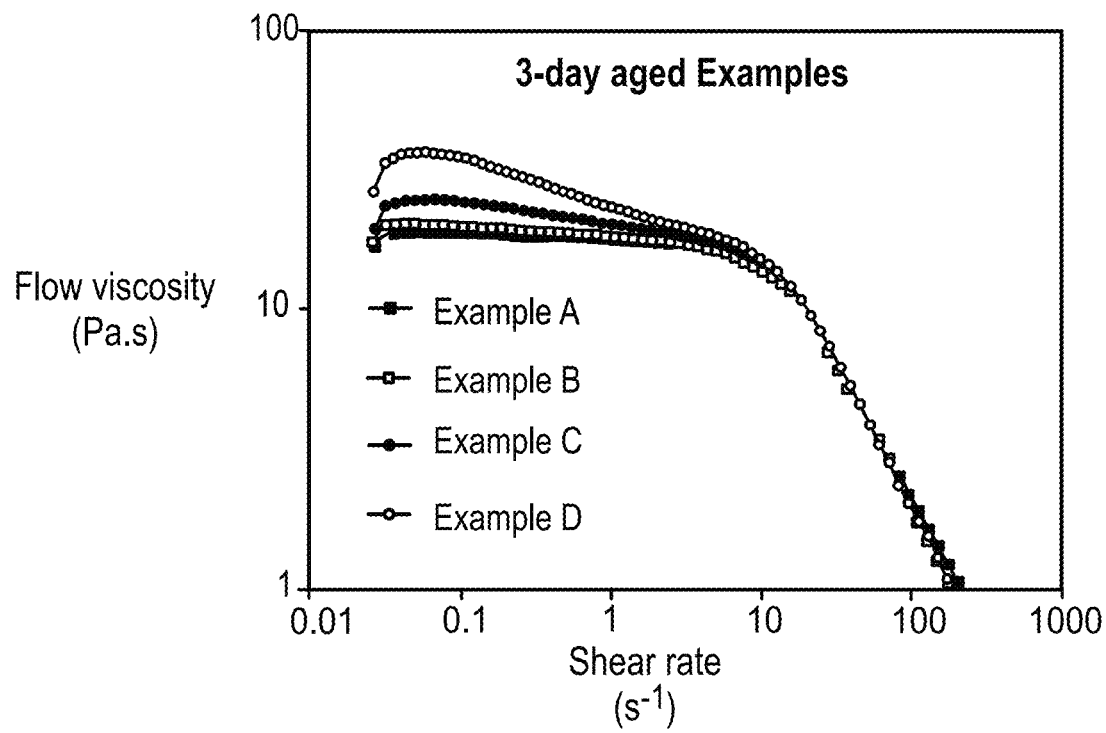

FIG. 4B demonstrates that even allowing the personal cleansing compositions to age 3 days at ambient temperature, the flow viscosity profile has not been altered. Hence, there is no apparent subsequent hydration of the natural polysaccharide or chemically modified natural polysaccharide that occurs after the initial processing.

Figure 4C:
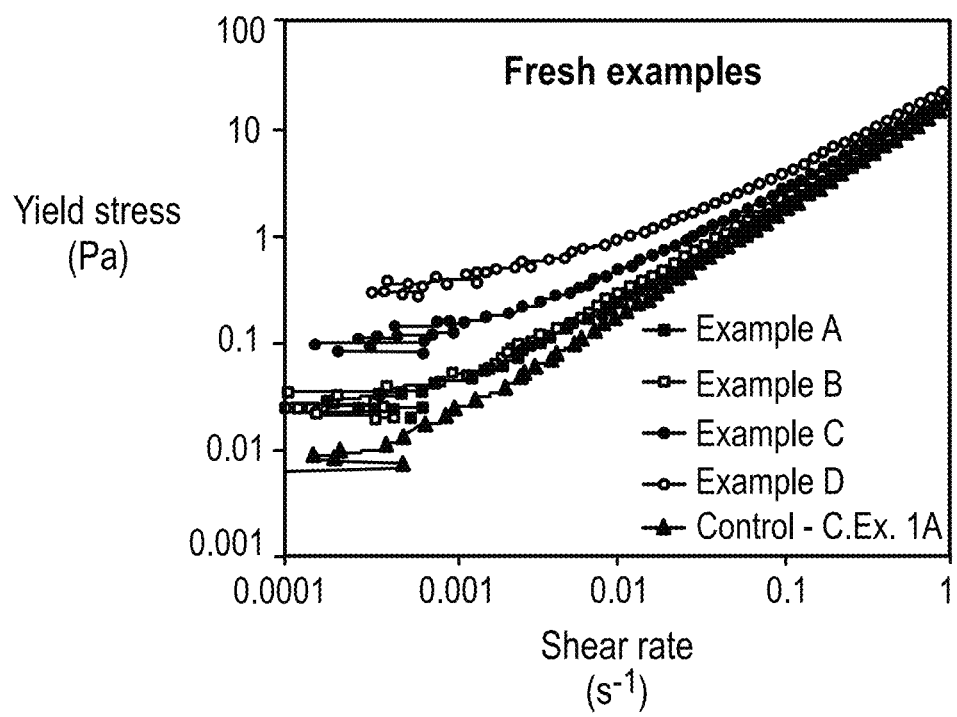
FIGS. 4C and 4D are related to the yield stress profile of personal cleansing compositions comprising xanthan gum added dry or added from a 5% aqueous solution to the composition, respectively upon preparation of the compositions or after 3 days aging at ambient temperature.
Figure 4D:
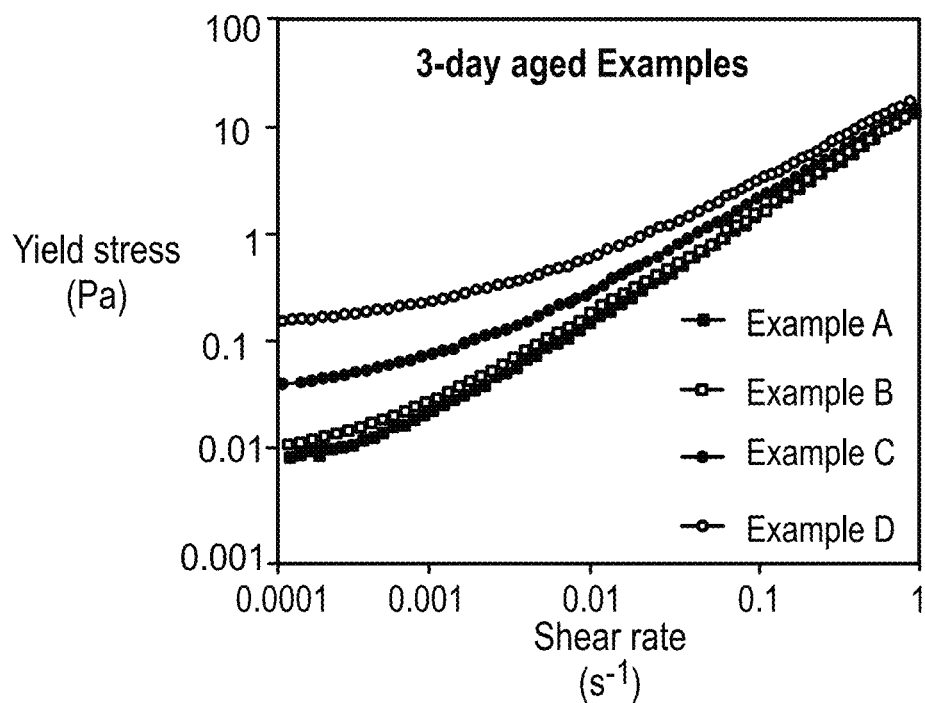

FIGS. 4C and 4D are related to the yield stress profile of personal cleansing compositions comprising xanthan gum added dry or added from a 5% aqueous solution to the composition, respectively upon preparation of the compositions or after 3 days aging at ambient temperature.

In FIG. 4C, when xanthan gum is added from a 5% aqueous solution (Examples C and D), a significant enhancement of the yield stress is obtained than when xanthan gum is added dry (Examples A and B). It is assumed that the pre-solubilization of the natural polysaccharide polymer can also improve the yield stress profile of the personal cleansing composition. Improving the yield stress profile of the personal cleansing composition can help to improve the stability of the composition.

FIG. 4D demonstrates that even allowing the personal cleansing compositions to age 3 days at ambient temperature, the yield stress profile has not been altered. Hence, the structure provided by the polymer liquid crystals forms a network that is stable after its initial formation.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal cleansing composition comprising:
   (a) a surfactant system, comprising about 0.1% to about 5% of a fatty acyl isethionate surfactant, by weight of the composition, and about 0.5% to about 40%, by weight of the composition of a fatty acyl sarcosinate;
   (b) about 0.25% to about 2%, by weight of the composition, of one or more natural polysaccharides; wherein one or more natural polysaccharides are chosen from xanthan gum, carrageenan gum, xanthan gum/locust bean gum, xanthan gum/guar gum, or mixtures thereof;
   (c) about 0.5% to about 3% of an electrolyte chosen from sodium or potassium citrate, calcium chloride, calcium bromide, zinc chloride, barium chloride, calcium nitrate, potassium chloride, sodium chloride, potassium iodide, sodium bromide, ammonium bromide, sodium sulfate, or mixtures thereof;

(d) water;

(e) an isotropic and micellar surfactant phase that includes the surfactant system; and (f) a polymer liquid crystalline phase comprising the natural polysaccharide, wherein the composition is free of from alkyl sulfate and alkyl ether sulfate types of surfactants, has a yield stress $\tau_y$ of 0.005 to 3 Pa according to the Herschel-Bulkley Rheology Test Method, a flow viscosity of 3 Pa·s to 100 Pa·s at 25° C. at a shear rate of 1.5 s$^{-1}$ according to the Flow Viscosity Test Method, and a transmittance at 25° C. and 640 nm of 25% to 90% according to the Optical Clarity Test Method.

2. The personal cleansing composition of claim 1, wherein the polymer liquid crystals further comprise one ingredient of the surfactant system.

3. The personal cleansing composition of claim 1, wherein the natural polysaccharide or the chemically modified natural polysaccharide is present in the polymer liquid crystalline phase at a level from about 1% to about 30% by total weight of the polymer liquid crystalline phase.

4. The personal cleansing composition of claim 1, wherein the fatty acyl isethionate surfactant is an isethionate according to the general Formula (I):

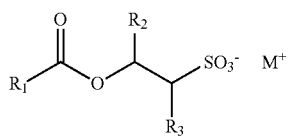

(I)

wherein $R_1$ is a saturated or unsaturated, straight or branched, alkyl or alkenyl chain with from 6 to 30 carbon atoms, $R_2$ and $R_3$ are each independently H or ($C_1$-$C_4$) alkyl, and M$^+$ is an alkali metal; or M$^+$ is an alkali-earth metal; or M$^+$ is an ammonium or a substituted ammonium cation.

5. The personal cleansing composition of claim 1, wherein the fatty acyl sarcosinate is a sarcosinate according to the general formula (II):

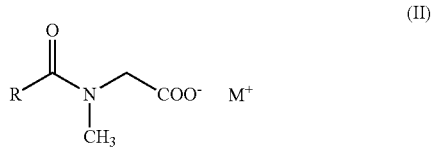

(II)

wherein R is a saturated or unsaturated, straight or branched or alkenyl, and M$^+$ is H, a sodium, potassium or ammonium cation.

6. The personal composition of claim 1, wherein the composition exhibits a yield stress value $\tau_y$, from about 0.005 Pa to about 3 Pa according to the Herschel-Bulkley Rheology Test Method.

7. The personal composition of claim 1, wherein the composition exhibits a flow viscosity from about 3 Pa·s to about 100 Pa·s at 25° C. at a shear rate of 1.5 s$^{-1}$ according to the Flow Viscosity Test Method.

* * * * *